(12) United States Patent
Phipps et al.

(10) Patent No.: US 9,750,749 B2
(45) Date of Patent: Sep. 5, 2017

(54) METHODS OF TREATING THYROID EYE DISEASE

(71) Applicants: Richard P. Phipps, Pittsford, NY (US); Naxin Guo, Rochester, NY (US); Steven Feldon, Rochester, NY (US)

(72) Inventors: Richard P. Phipps, Pittsford, NY (US); Naxin Guo, Rochester, NY (US); Steven Feldon, Rochester, NY (US)

(73) Assignee: University of Rochester, Rochester, NY (US)

(*) Notice: Subject to any disclaimer, the term of this patent is extended or adjusted under 35 U.S.C. 154(b) by 0 days.

(21) Appl. No.: 15/061,727

(22) Filed: Mar. 4, 2016

(65) Prior Publication Data

US 2016/0199386 A1 Jul. 14, 2016

Related U.S. Application Data

(62) Division of application No. 13/099,991, filed on May 3, 2011, now Pat. No. 9,320,723.

(60) Provisional application No. 61/330,742, filed on May 3, 2010.

(51) Int. Cl.
| | |
|---|---|
| *A61K 31/4439* | (2006.01) |
| *A61K 31/506* | (2006.01) |
| *A61K 31/519* | (2006.01) |
| *A61K 31/557* | (2006.01) |
| *A61K 31/166* | (2006.01) |
| *A61K 31/403* | (2006.01) |
| *A61K 31/5575* | (2006.01) |
| *A61K 31/7105* | (2006.01) |
| *C12N 15/113* | (2010.01) |
| *A61K 31/201* | (2006.01) |
| *A61K 31/713* | (2006.01) |
| *A61K 9/00* | (2006.01) |

(52) U.S. Cl.
CPC ......... *A61K 31/557* (2013.01); *A61K 31/166* (2013.01); *A61K 31/201* (2013.01); *A61K 31/403* (2013.01); *A61K 31/4439* (2013.01); *A61K 31/506* (2013.01); *A61K 31/519* (2013.01); *A61K 31/5575* (2013.01); *A61K 31/713* (2013.01); *A61K 31/7105* (2013.01); *C12N 15/1137* (2013.01); *A61K 9/0048* (2013.01); *C12N 2310/14* (2013.01); *C12N 2320/31* (2013.01); *Y10S 514/912* (2013.01)

(58) Field of Classification Search
None
See application file for complete search history.

(56) References Cited

U.S. PATENT DOCUMENTS

| | | | |
|---|---|---|---|
| 2003/0096317 A1 | 5/2003 | Smith et al. | |
| 2007/0286856 A1 | 12/2007 | Brown et al. | |
| 2008/0227782 A1* | 9/2008 | Aldous | C07D 239/28 514/235.8 |
| 2008/0300217 A1 | 12/2008 | Nilsson | |
| 2010/0119609 A1 | 5/2010 | Dobak | |
| 2012/0077857 A1 | 3/2012 | Wang et al. | |
| 2012/0190695 A1* | 7/2012 | Vandeusen | C07D 271/06 514/256 |

FOREIGN PATENT DOCUMENTS

| | | | | |
|---|---|---|---|---|
| GB | WO 2006053390 A1 * | 5/2006 | ........... | A61K 31/196 |
| WO | 2004082610 | 9/2004 | | |

OTHER PUBLICATIONS

Ikai et al., Inhibitory effect of tranilast on prostaglandin D synthetase, Biochem Pharmacol. Aug. 15, 1989;38(16):2673-6, printed from http://www.ncbi.nlm.nih.gov/pubmed/2475113, 1 page, Abstract only.*

Lang, Ocular drug delivery conventional ocular formulations, Advanced Drug Delivery Reviews, 16 (1995) 39-43.*

Guo et al., Mast cell-derived prostaglandin D2 controls hyaluronan synthesis in human orbital fibroblasts via DP1 activation: implications for thyroid eye disease, J Biol Chem. May 21, 2010;285(21):15794-804. Epub Mar. 22, 2010, abstract only, 2 pages.*

Feldon et al., "Activated Human T Lymphocytes Express Cyclooxygenase-2 and Produce Proadipogenic Prostaglandins that Drive Human Orbital Fibroblast Differentiation to Adipocytes," Am. J. Path. 169(4):1183-1193 (2006).

Gianoukakis et al., "Hyaluronan Accumulation in Thyroid Tissue: Evidence for Contributions from Epithelial Cells and Fibroblasts," Endocrinology 148:54-62 (2007).

Guo et al., "A PPARgamma Endogenous Ligand 15-deoxy-Delta12,14-Prostaglandin J2 Inhibits TGF-beta-mediated Responses in Human Orbital Fibroblasts," Presentation Abstract, Association for Research in Vision and Ophthalmology 2011 Annual Meeting, Fort Lauderdale, Florida, May 4, 2011 (2011).

Guo et al., "Prostaglandin D2 Stimulates Hyaluronan Synthesis Through the DP1 Receptor in Human Orbital Fibroblasts," Presentation Abstract for Poster 1454/A344, Association for Research in Vision and Ophthalmology 2009 Annual Meeting, Fort Lauderdale, Florida, May 4, 2009 (2009).

Guo et al., "Prostaglandin D2 Stimulates Hyaluronan Synthesis Through the DP1 Receptor in Human Orbital Fibroblasts," Poster Presentation 1454/A344, Association for Research in Vision and Ophthalmology 2009 Annual Meeting, Fort Lauderdale, Florida, May 4, 2009 (2009).

(Continued)

*Primary Examiner* — Gigi Huang
(74) *Attorney, Agent, or Firm* — LeClairRyan, a Professional Corporation

(57) ABSTRACT

The present invention relates to a methods and compositions for the treatment of and management of symptoms for thyroid eye disease. The methods include administering to a patient having thyroid eye disease an agent that interferes with hyaluronan synthesis in an amount that is effective to inhibit hyaluronan synthesis in a retro-ocular space. The pharmaceutical compositions that includes a carrier suitable for ophthalmic delivery and an agent that interferes with hyaluronan synthesis. Combination therapies are also disclosed.

5 Claims, 19 Drawing Sheets

(56) References Cited

OTHER PUBLICATIONS

Kuriyan et al., "Improvement of Thyroid Eye Disease Following Treatment with the Cyclooxygenase-2 Selective Inhibitor Celecoxib," Thyroid 18(8):911-914 (2008).
Lehmann et al., "Immune Mechanisms in Thyroid Eye Disease," Thyroid 18(9):959-965 (2008).
Lehmann et al., "Regulation of Lymphocyte Function by PPARgamma: Relevance to Thyroid Eye Disease-Related Inflammation," PPAR Res. 2008:Article ID 895901, 12 pages (2008).
Smith et al., "Immunoglobulins from Patients with Graves' Disease Induce Hyaluronan Synthesis in Their Orbital Fibroblasts Through the Self-Antigen, Insulin-Like Growth Factor-1 Receptor," J. Clin. Endocrinol. Metab. 89:5076-5080 (2004).
Qin et al., "PPARS in Eye Biology and Disease," Editorial, PPAR Res. 2008:Article ID 518790, 2 pages (2008).
PPARS in Eye Biology and Disease, PPAR Res. (Qin & Chuck eds. 2008) (table of contents only).
Guo et al., "PPARgamma Ligands Inhibit TGF-beta Induced, Hyaluronan Dependent, T Cell Adhesion to Orbital Fibroblasts," J. Biol. Chem. Manuscript M110.179317, available at http://www.jbc.org/cgi/doi/10.1074/jbc.M110.179317 (2011).
Guo et al., "Mast Cell-Derived Prostaglandin D2 Controls Hyaluronan Synthesis in Human Orbital Fibroblasts via DP1 Activation. Implications for Thyroid Eye Disease," J. Biol. Chem. 285(21):15794-15804 (2010).
Nielsen et al., "B-cell depletion with rituximab in the treatment of autoimmune diseases. Graves' ophthalmopathy the latest addition to an expanding family," Expert Opin Bioi Ther. 7(7) (Jul. 2007), printed from http://www.ncbi.nlm.nih.gov/pubmed/17665994, Abstract only.
Winfield, Pharmaceutical Practice, Ophthalmic Products, Churchill Livingstone, 2004, 264-279.
www.mayoclinic.com, Graves' Disease, Jul. 1, 2008, printed from http://web.archive.org/web/20080701214625/http://www.mayoclinic.com/health/graves-disease/DS00181/DSECTION=causes, 6 pages.

\* cited by examiner

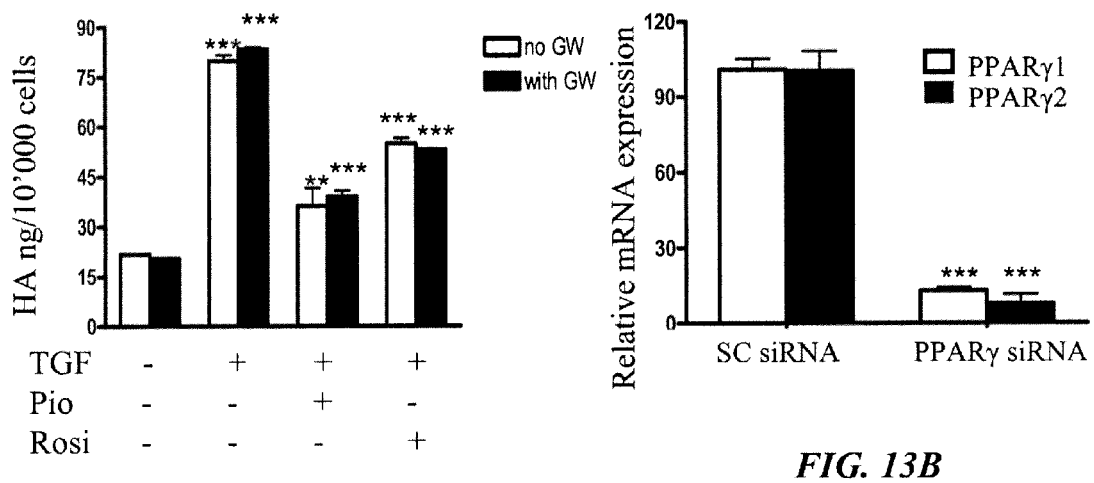
*FIG. 13A*
*FIG. 13B*
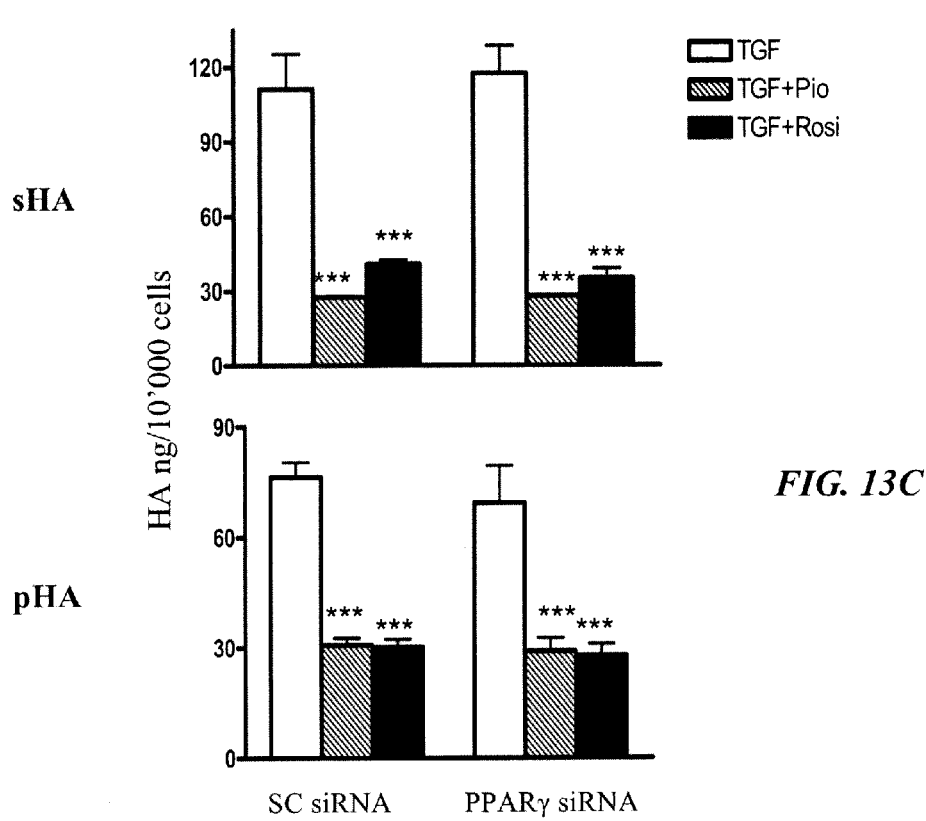
*FIG. 13C*

FIG. 14A
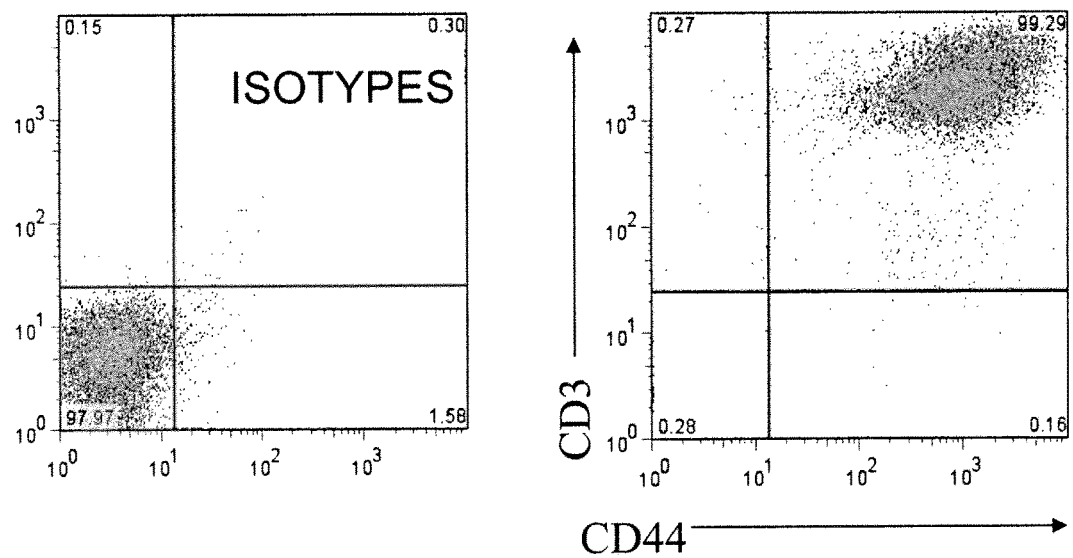
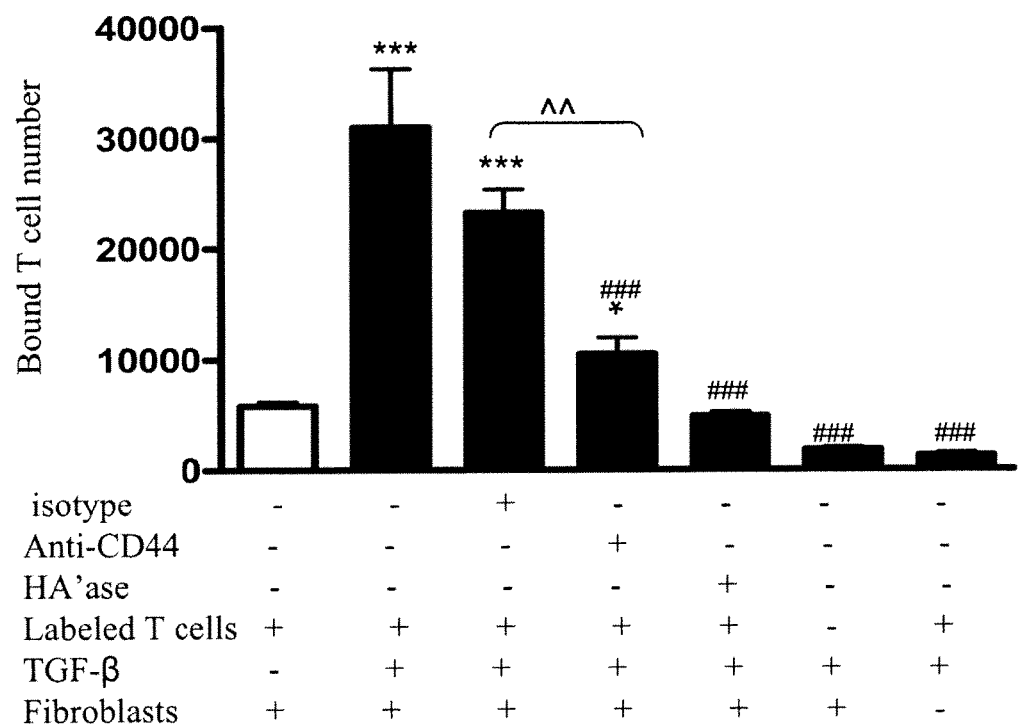
FIG. 14B ically ocular space (Smith et al., *J Clin Endocrinol Metab* 89(10):5076-5080 (2004)), resulting in the disfigurement and vision impairment (Kuriyan et al., *Curr Opin Ophthalmol* 19(6):499-506 (2008)) characteristic of TED.

SEQUENCE LISTING

```
<160> NUMBER OF SEQ ID NOS: 18

<210> SEQ ID NO 1
<211> LENGTH: 19
<212> TYPE: RNA
<213> ORGANISM: Artificial
<220> FEATURE:
<223> OTHER INFORMATION: RNAi specific for HAS2

<400> SEQUENCE: 1
uuggaaccac acucuuugg                                            19

<210> SEQ ID NO 2
<211> LENGTH: 19
<212> TYPE: RNA
<213> ORGANISM: Artificial
<220> FEATURE:
<223> OTHER INFORMATION: RNAi specific for HAS2

<400> SEQUENCE: 2
ccaaagagug ugguuccuu                                            19

<210> SEQ ID NO 3
<211> LENGTH: 20
<212> TYPE: DNA
<213> ORGANISM: Artificial
<220> FEATURE:
<223> OTHER INFORMATION: Sense primer
```

```
<400> SEQUENCE: 3
aaagaagccg acactaaacc                                              20

<210> SEQ ID NO 4
<211> LENGTH: 20
<212> TYPE: DNA
<213> ORGANISM: Artificial
<220> FEATURE:
<223> OTHER INFORMATION: Antisense primer

<400> SEQUENCE: 4
cttccattac ggagagatcc                                              20

<210> SEQ ID NO 5
<211> LENGTH: 19
<212> TYPE: DNA
<213> ORGANISM: Artificial
<220> FEATURE:
<223> OTHER INFORMATION: Sense primer

<400> SEQUENCE: 5
gcgattcctt cactgatac                                               19

<210> SEQ ID NO 6
<211> LENGTH: 20
<212> TYPE: DNA
<213> ORGANISM: Artificial
<220> FEATURE:
<223> OTHER INFORMATION: Anitsense primer

<400> SEQUENCE: 6
cttccattac ggagagatcc                                              20

<210> SEQ ID NO 7
<211> LENGTH: 21
<212> TYPE: DNA
<213> ORGANISM: Artificial
<220> FEATURE:
<223> OTHER INFORMATION: Has1 Forward Primer

<400> SEQUENCE: 7
tgtgtatcct gcatcagcgg t                                            21

<210> SEQ ID NO 8
<211> LENGTH: 26
<212> TYPE: DNA
<213> ORGANISM: Artificial
<220> FEATURE:
<223> OTHER INFORMATION: Has1 Reverse Primer

<400> SEQUENCE: 8
ctggaggtgt acttggtagc ataacc                                       26

<210> SEQ ID NO 9
<211> LENGTH: 20
<212> TYPE: DNA
<213> ORGANISM: Artificial
<220> FEATURE:
<223> OTHER INFORMATION: Has2 Forward Primer

<400> SEQUENCE: 9
gcctcatctg tggagatggt                                              20

<210> SEQ ID NO 10
<211> LENGTH: 20
```

```
<212> TYPE: DNA
<213> ORGANISM: Artificial
<220> FEATURE:
<223> OTHER INFORMATION: Has2 Reverse Primer

<400> SEQUENCE: 10
atgcactgaa cacacccaaa                                              20

<210> SEQ ID NO 11
<211> LENGTH: 20
<212> TYPE: DNA
<213> ORGANISM: Artificial
<220> FEATURE:
<223> OTHER INFORMATION: Has3 Forward Primer

<400> SEQUENCE: 11
ggcattatca aggccaccta                                              20

<210> SEQ ID NO 12
<211> LENGTH: 20
<212> TYPE: DNA
<213> ORGANISM: Artificial
<220> FEATURE:
<223> OTHER INFORMATION: Has3 Reverse Primer

<400> SEQUENCE: 12
aggccaatga agttcaccac                                              20

<210> SEQ ID NO 13
<211> LENGTH: 20
<212> TYPE: DNA
<213> ORGANISM: Artificial
<220> FEATURE:
<223> OTHER INFORMATION: DP1 Forward Primer

<400> SEQUENCE: 13
tctgcgcgct acctttcatg                                              20

<210> SEQ ID NO 14
<211> LENGTH: 21
<212> TYPE: DNA
<213> ORGANISM: Artificial
<220> FEATURE:
<223> OTHER INFORMATION: DP1 Reverse Primer

<400> SEQUENCE: 14
tcctcgtgga ccatctggat a                                            21

<210> SEQ ID NO 15
<211> LENGTH: 20
<212> TYPE: DNA
<213> ORGANISM: Artificial
<220> FEATURE:
<223> OTHER INFORMATION: DP2 Forward Primer

<400> SEQUENCE: 15
tttctcaaca tgttcgccag                                              20

<210> SEQ ID NO 16
<211> LENGTH: 20
<212> TYPE: DNA
<213> ORGANISM: Artificial
<220> FEATURE:
<223> OTHER INFORMATION: DP2 Reverse Primer

<400> SEQUENCE: 16
```

```
aagcaccagg cagactttgt                                              20

<210> SEQ ID NO 17
<211> LENGTH: 20
<212> TYPE: DNA
<213> ORGANISM: Artificial
<220> FEATURE:
<223> OTHER INFORMATION: 7S RNA Forward Primer

<400> SEQUENCE: 17
accaccaggt tgcctaagga                                              20

<210> SEQ ID NO 18
<211> LENGTH: 20
<212> TYPE: DNA
<213> ORGANISM: Artificial
<220> FEATURE:
<223> OTHER INFORMATION: 7S RNA Reverse Primer

<400> SEQUENCE: 18
cacgggagtt ttgacctgct                                              20
```

METHODS OF TREATING THYROID EYE DISEASE

This application is a divisional of U.S. patent application Ser. No. 13/099,991, filed May 3, 2011, and claims the benefit of U.S. Provisional Patent Application Ser. No. 61/330,742, filed May 3, 2010, which are hereby incorporated by reference in their entirety.

This invention was made with government support under grant number EY017123 awarded by the National Institutes of Health. The government has certain rights in this invention.

FIELD OF THE INVENTION

The present invention relates to methods and compositions for the treatment of Thyroid Eye Disease.

BACKGROUND OF THE INVENTION

Graves' disease is an autoimmune disorder in which 40-60% of patients develop Graves' ophthalmopathy, also called Thyroid Eye Disease (TED). TED is characterized by expansion of the orbital fat compartment and extraocular muscles (Prabhakar et al., *Endocr Rev* 24(6):802-835 (2003)). Intense inflammation and infiltration of immune cells, including T cells, macrophages and mast cells, in the retrobulbar space of TED patients are key factors that drive the proliferation and differentiation of orbital fibroblasts to adipocytes (Lehmann et al., *PPAR Res*, Art. ID. 895901 (2008); Feldon et al., *Am J Pathol* 169(4):1183-1193 (2006)). In addition to the adipogenic potential of orbital fibroblasts, these cells are also key producers of extracellular matrix glycosaminoglycans (GAG). One of the key pathological findings in TED patients is the over-production and accumulation of the GAG hyaluronan (HA). The extremely hydrophilic nature of HA leads to remarkable increases in tissue volume and to the anterior displacement of the eye, or exophthalmos (Smith et al., *J Clin Endocrinol Metab* 89(10):5076-5080 (2004)), resulting in the disfigurement and vision impairment (Kuriyan et al., *Curr Opin Ophthalmol* 19(6):499-506 (2008)) characteristic of TED.

HA is synthesized as an acidic, negatively charged, high molecular weight polysaccharide via the actions of hyaluronan synthases (HAS) (Jiang et al., *Annu Rev Cell Dev Biol* 23:435-461 (2007)), of which there are three isoforms: HAS1, HAS2 and HAS3. Increased HA synthesis closely correlates with the expression levels of HAS (Makkonen et al., *J Biol Chem* 284(27):18270-18281 (2009)), which are themselves induced by growth factors, cytokines (Makkonen et al., *J Biol Chem* 284(27):18270-18281 (2009); Campo et al., *Br J Biomed Sci* 66(1):28-36 (2009); Guo et al., *J Biol Chem* 282(17):12475-12483 (2007)) and prostaglandins (PG) (Honda et al., "Prostaglandin E2 Stimulates Cyclic AMP-mediated Hyaluronan Synthesis in Rabbit Pericardial Mesothelioma Cells," *Biochem J.* 292:497-505 (1993); Fischer et al., *Thromb Haemost* 98(2)287-295 (2007)). One PG that may have an important implication in TED is $PGD_2$. $PGD_2$ is a metabolite of arachidonic acid that is formed by the actions of cyclooxygenases (Cox) and $PGD_2$ synthases (PGDS) (Goetzl et al., *Faseb J* 9(11):1051-1058 (1995); Herlong et al., *Immunol Lett* 102(2):121-131 (2006)). Many of the biological actions of $PGD_2$ are mediated through two G protein-coupled receptors, DP receptor 1 (DP1) and DP2 (also called chemoattractant receptor-homologous molecule (CRTH2)) (Boie et al., *J Biol Chem* 270(32):18910-18916 (1995); Nagata et al., *FEBS Lett* 459 (2):195-199 (1999); Kostenis et al., *Trends Mol Med* 12(4): 148-158 (2006)). These receptors elicit divergent effects by the coupling to either Gs (DP1) or Gi (DP2) to elevate cyclic AMP (cAMP) or intracellular calcium ($Ca^{2+}$), respectively. $PGD_2$ can also spontaneously undergo a series of dehydration reactions to form the PGJ family of prostaglandins, including $15d-PGJ_2$, an endogenous ligand for the peroxisome proliferator-activated receptor (PPARγ) (Forman et al., *Cell* 83(5):803-812 (1995); Kliewer et al., *Cell* 83(5):813-819 (1995)).

Human orbital fibroblasts express PPARγ and PPARγ is crucial for the differentiation of fibroblasts to adipocytes. A recent publication reported that activated human T lymphocytes isolated from patients with TED produce much more $PGD_2$-derived PGs compared to T cells from healthy individuals (Feldon et al., *Am J Pathol* 169(4):1183-1193 (2006)). Mast cells are also a key cellular source of PGs, with $PGD_2$ being the major prostanoid released (Feldon et al., *Am J Pathol* 169(4):1183-1193 (2006); Lewis et al., *J Immunol* 129(4):1627-1631 (1982)). Mast cells are a central immune cell in the pathogenesis of TED. Not only is there intense mast cell infiltration and degranulation (Lauer et al., *Ophthal Plast Reconstr Surg* 24(4):257-261 (2008)) associated with adipocytes (Boschi et al., *Br J Ophthalmol* 89(6): 724-729 (2005)) in TED patients, but co-culture of mast cells with orbital fibroblasts up-regulates HA synthesis (Smith et al., *Endocrinology* 140(8):3518-3525 (1999)). It remains unknown whether this increase in HA production by orbital fibroblasts is the result of $PGD_2$ acting via the direct modulation of DP receptors or via some other means. Further, it would be desirable to identify therapies for TED that can reliably decrease HA production within the retro-ocular space.

The present invention is directed to overcoming these and other limitations in the art.

SUMMARY OF THE INVENTION

A first aspect of the present invention relates to a method of treating thyroid eye disease that includes administering to a patient having thyroid eye disease an agent that interferes with hyaluronan synthesis in an amount that is effective to inhibit hyaluronan synthesis in a retro-ocular space.

A second aspect of the present invention relates to a pharmaceutical composition that includes a carrier suitable for ophthalmic delivery and an agent that interferes with hyaluronan synthesis.

The accompanying examples demonstrate for the first time that $PGD_2$ increases HA synthesis in orbital fibroblasts via the induction of HAS2. Pharmacological inhibition of DP1, but not DP2, prevented the $PGD_2$-induced up-regulation of HA. It is also demonstrated that inhibition of $PGD_2$ synthesis by mast cells prevents HA synthesis by orbital fibroblasts. These results have important implications for therapies directed against treating those afflicted with TED. Preventing $PGD_2$ synthesis by mast cells and/or DP1 activation on orbital fibroblasts can reduce the severity of the disease. In addition, the accompanying examples demonstrate that the PPARγ ligands pioglitazone (Pio) and rosiglitazone (Rosi) suppress TGF-β-induced HA production and HAS activation in human orbital fibroblasts, but quite unexpectedly through PPARγ-independent pathways. Pio and Rosi also attenuate TGF-β-mediated T cell adhesion to orbital fibroblasts by decreasing HA synthesis. Together, these data confirm that various agents that interfere with HA synthesis, particularly HA synthesis via HAS2 or DP1 signaling, can be used to treat TED or control symptoms thereof.

BRIEF DESCRIPTION OF THE DRAWINGS

FIG. 1C shows an agarose gel HA analysis. Orbital fibroblasts (OF1 and OF2) were cultured in RPMI-1640 with 2% FBS for 3 days and then treated with 5 μM $PGD_2$ ($D_2$) or vehicle (V) for 18 hours and the conditioned media analyzed by agarose gel electrophoresis. Both OF1 and OF2 exhibited basal HA (Lanes 3 and 5, respectively, blue color). When treated with $PGD_2$, there was an increase in color intensity, indicating increased HA production (Lanes 4 and 6, compare with Lanes 3 and 5). *Streptomyces* hyaluronidase-digested sample (HA'ase) (from $PGD_2$-treated OF2) was included as a negative control (Lane 7).

FIG. 3A shows the results of RT-PCR analysis: cDNA from orbital fibroblasts treated with 5 μM $PGD_2$ or vehicle for 2 hours was amplified by RT-PCR and separated on 5% acrylamide gels. All three HAS isoforms are expressed in human orbital fibroblasts. Following treatment with $PGD_2$, there was a relative increase in the abundance of HAS1, HAS2 and HAS3 mRNA. 7S was used as a control. B. qRT-PCR: Total RNA from orbital fibroblasts treated with 5 μM $PGD_2$ from 1 to 24 hours was analyzed by qRT-PCR as described in the accompanying Examples. There was a significant increase in HAS mRNA levels (HAS1, HAS2 and HAS3) beginning at 2 hours (***$p<0.001$ compared to time 0 for each HAS isoform). Of the three, HAS1 yielded the greatest increase (2807±213) (FIG. 3B); this increase in HAS1 was significantly greater than HAS2 or HAS3 (###$p<0.001$) (compare to FIGS. 3C-D). Expression of HAS1 and HAS2 remained significantly elevated through 4 hours (*$p<0.05$) (FIGS. 3B-C). By 16 hours, mRNA for HAS1, HAS2 and HAS3 was not different from control. Results are expressed as the mean±SD of triplicate samples performed on duplicate cultures.

FIG. 5A illustrates the results of RT-PCR: Human orbital fibroblasts (OF1 and OF2) and T cells express DP1 and DP2 mRNA. Note the variability in the expression of DP2 between the two fibroblast strains. FIG. 5B is a Western blot analysis, which revealed that orbital fibroblasts and T cells express both DP1 and DP2 protein. Membranes were re-probed for GAPDH to ensure equal protein loading. FIG. 5C is a graph illustrating that pharmacological inhibition of DP1, but not DP2, blocks $PGD_2$ and $PGJ_2$ induced HA production. Orbital fibroblasts were left untreated (vehicle) or were pre-treated with 100 nM of the DP1 antagonist MK-0524 (MK) or DP2 antagonist Ramatroban (RAM) for 1 hour with or without $PGD_2$ or $PGJ_2$ for 18 hours and HA ELISA performed. Both $PGD_2$ and $PGJ_2$ significantly increased HA production compared to untreated (vehicle) (###$p<0.001$, ##$p<0.01$, respectively). Pre-treatment of orbital fibroblasts with MK significantly decreased the ability of $PGD_2$ (**$p<0.01$) and $PGJ_2$ (*$p<0.05$) to induce HA levels. RAM was not able to prevent $PGD_2$- and $PGJ_2$-increased HA levels (#$p<0.05$, ##$p<0.01$ compared to vehicle control, respectively); ns=not significant compared to untreated (vehicle). FIGS. 5D-F are graphs illustrating the effect of treatment with the DP1 agonist BW245C on increased expression of HAS mRNA. Orbital fibroblasts were cultured in reduced serum for three days and exposed to BW245C (10 μM) for the indicated times. There was a significant increase in HAS1 (fold increase: 329±128; $p<0.01$) (FIG. 5D) and HAS2 (fold increase 17±0.14; *$p<0.001$) (FIG. 5E) at two hours compared to vehicle control. HAS3 mRNA increased by 6 hours (4.8±0.06; ***$p<0.01$) (FIG. 5F). FIG. 5G is a graph showing that activation of DP1 by the selective agonist BW245C induces HA. There was a significant increase in HA when fibroblasts were treated with 5 and 10 μM BW245C (*$P<0.05$, **$P<0.01$) compared to vehicle control. Samples were run in duplicate utilizing three separate human orbital fibroblast strains (representative results are shown).

FIG. 6A shows that DP1 activation by $PGD_2$ or BW245C increases intracellular cAMP level. Orbital fibroblasts were treated with $PGD_2$ or BW245C for up to 60 minutes and intracellular cAMP detected as described in the Experimental Procedures. There was a significant increase in cAMP within 15 minutes of treatment with $PGD_2$ compared to vehicle control (*p<0.05). cAMP further increased by 30 and 60 minutes (***p<0.001). FIG. 6B shows the ELISA results following treatment with forskolin or IBMX, with or without $PGD_2$ or PGJ2. Cultures of confluent orbital fibroblasts were treated with 5 µM forskolin or 200 µM IBMX, with or without 5 µM $PGD_2$ or 2 µM $PGJ_2$, for 18 hours and the cell culture supernatant collected for HA ELISA. There was a significant increase in HA when cells were treated with forskolin, $PGD_2$ or $PGJ_2$ compared to vehicle-treated (open bar) (*p<0.05, **p<0.01). Augmenting cAMP (via IBMX) in conjunction with $PGD_2$ or $PGJ_2$ significantly increased HA when compared to $PGD_2$ and $PGJ_2$ alone (#p<0.05). Results are expressed as the mean±SD.

FIG. 7A is a Western blot of HMC-1 cells, which indicates the expression of Cox-1 and H-PGDS. Unactivated HMC-1 cells do not express Cox-2. GAPDH was used as a housekeeping protein. FIG. 7B is a graph showing that inhibition of H-PGDS activity ameliorates the production of $PGD_2$ by activated mast cells. HMC-1 cells were treated with HQL-79 for 1 hour, followed by activation with A23187 and cell culture supernatant assessed for $PGD_2$ levels by commercial EIA. Activation of HMC-1 cells with A23187 significantly increased $PGD_2$ production (###, p<0.001, compared to untreated). Inclusion of HQL-79 significantly reduced $PGD_2$ production (***, p<0.001).

FIG. 8A is a graph showing the effects of contact co-culture. Confluent orbital fibroblasts were seeded with HMC-1 cells at a cell ratio of 1:1 for 4 h. The mast cells were then removed, the fibroblasts were washed, and fresh media was added for another 18 hours. The media was collected for HA ELISA. Co-culture of orbital fibroblasts with HMC-1 cells significantly increase HA synthesis (, p<0.001). FIG. 8B is a graph showing the effects of transwell co-culture. HMC-1 cells and confluent fibroblasts were co-cultured in a transwell system, where the fibroblasts and HMC-1 cells were separated by a 0.4 µm membrane; the HMC-1: orbital fibroblast (OF) ratio was: 5:1, 10:1 or 20:1. The conditioned media from both chambers was collected for HA ELISA. There was a significant difference in HA levels between HMC-1 (upper chamber, open bars) and orbital fibroblasts (lower chamber, black bars) (#p<0.05; ###p<0.001). Co-culture of orbital fibroblasts with HMC-1 cells significantly increased HA production only by the fibroblasts (lower chamber) (*p<0.001 compared to no HMC-1 cells). FIG. 8C is a graph showing that inhibition of $PGD_2$ secretion by HMC-1 cells prevents HA production by orbital fibroblasts. HMC-1 cells were treated with the H-PGDS inhibitor HQL-79 prior to co-culturing (ratio 20:1) with orbital fibroblasts. There was a significant increase in HA synthesis when fibroblasts were cultured with HMC-1 cells (**p<0.01 compared to no HMC). This increase in HA was attenuated when $PGD_2$ production in mast cells was prevented by HQL-79 (##p<0.001, HQL-79 compared to vehicle).

FIG. 10B is a panel of images showing confluent orbital fibroblasts cultured in reduced serum for three days and treated with 2 ng/ml TGF-β1 for 24 hours. Cells were stained with biotinylated HABP (for HA, green, a, d, g), phalloidin (for F-actin, red, b, e, h) and DAPI (for nucleus, blue). Panels a-c: untreated cells; panels d-f: TGF-β1 treated cells; panels g-i: orbital fibroblasts were treated with HA'ase before fixation. Panels c, f, i; merged fluorescence with DAPI staining.

FIGS. 13A-C demonstrate that neither the irreversible PPARγ antagonist GW9662 nor PPARγ siRNA inhibit Pio and Rosi-mediated suppression of HA synthesis. FIG. 13A is a graph illustrating relative HA expression from primary orbital fibroblasts pretreated with 1 μM GW9662 for 1 hour or left untreated, and then treated with 2 ng/ml TGF-β1 and either 10 μM Pio, or 10 μM Rosi for 24 hours. HA synthesis was analyzed by ELISA. GW9662 does not restore TGF-β stimulated HA synthesis in cells treated with Pio or Rosi. Results shown are representative of 3 independent experiments. $p<0.01$, *$p<0.001$ compared to TGF-β1 treatment. FIG. 13B is a graph showing relative PPARγ mRNA expression in orbital fibroblast cultures transfected with PPARγ SMARTpool siRNAs or non-specific control siRNA. Forty-eight hours after transfection, the medium was changed and culture continued for 2 days. Total RNA was collected and PPARγ 1 and PPARγ 2 mRNA levels were analyzed by qRT-PCR and normalized to 7S RNA. Results shown are the mean±SD for two independent experiments with triplicate cultures in each experiment. ***$p<0.001$, compared to scramble siRNA. FIG. 13C contains a pair of graphs showing the PPARγ independent mechanism of Pio and Rosi. PPARγ siRNA transfected orbital fibroblast cultures were serum starved and then treated with TGF-β1 with or without 10 μM Pio or 10 μM Rosi. Twenty-four hours after treatment, the conditioned medium and cell trypsin solution were collected and HA levels were analyzed by ELISA. Results shown are the mean±SD for three independent experiments with duplicate cultures in each experiment.

FIGS. 14A-B illustrates that TGF-β1 induces human peripheral blood T cell adhesion to orbital fibroblasts through HA-CD44 interaction. FIG. 14A shows the expression of CD3 and CD44 on PBMCs. PBMCs were incubated with CD3/CD28 beads in RPMI1640 with 10% FBS medium at 37° C. for 2 days. After that, rIL-2 (50 U/ml) was added to the culture and incubated for several days according to the cell number. After T-cell expansion, the expression of CD3 and CD44 on the cell surface was examined by flow-cytometry. More than 99% of the enriched cells express CD3 and CD44. FIG. 14B is a graph illustrating the number of T cells bound to TGF-β1 treated orbital fibroblasts. Enriched T cells were fluorescently labeled by incubation with calcein-AM. After labeling, some T cells were incubated with 40 μg/ml monoclonal CD44 antibody. Confluent orbital fibroblasts were cultured in reduced serum for three days and treated with 2 ng/ml TGF-β1 for 24 hours. In some cultures, orbital fibroblasts were treated with 100 mU/ml HA'ase for 1 hour. T cells were added and allowed to adhere for 90 min at 4° C. Plates were washed three times and fluorescence was measured at 535 nm. White bars, fibroblast vehicle control; black bars, fibroblast treated with TGF-β for 24 hours. There was a significant increase in T cell adhesion to TGF-β1 treated orbital fibroblasts (***$p<0.001$ compared to vehicle control). CD44 antibody attenuated and HA'ase completely abolished the adhesion of T cells to fibroblasts (###$p<0.001$ compared to TGF-β1 alone; ^^$p<0.01$ CD44 antibody versus isotype). Results are expressed as bound T cell number and are the mean±SEM (n=6) of one of four experiments.

FIG. 15A is a graph showing the effect of TGF-β1 on orbital fibroblasts, which were transfected with siRNA for HAS1, HAS2, or a scramble control (SC) siRNA as described in the accompanying Examples. The cells were serum starved in RPMI 1640 with 0.5% FBS and treated with 2 ng/ml TGF-β1 for 6 h, and HAS expression levels were analyzed by qRT-PCR. The mRNA for HAS1 and HAS2 in the TGF-β-treated SC siRNA samples was normalized to 100 for comparison of gene expression. Each siRNA reduced its target mRNA expression selectively and significantly (up to 80%). For HA detection in FIG. 15B, HAS1 or HAS2 siRNA transfected orbital fibroblasts were exposed to 2 ng/ml TGF-β1 for 24 h, and secreted HA and pericellular HA was analyzed by HA ELISA. Knockdown of HAS2, but not HAS1, significantly reduced both secreted HA and pericellular HA in human orbital fibroblasts. , $p<0.01$, *, $p<0.001$ compared with TGF-β-treated SC siRNA-transfected; AA, $p<0.01$, ^^^, $P<0.001$, HAS1 siRNA versus HAS2 siRNA-transfected, TGF-β-treated fibroblasts. FIG. 15C is a graph illustrating the relationship between HAS expression and TGF-β1 induced T cell adhesion to orbital fibroblasts. Orbital fibroblasts were transfected with siRNA for HAS1, HAS2, or a SC siRNA for 24 hours. Then cells were serum starved in RPMI 1640 with 0.5% FBS and treated with 2 ng/ml TGF-β1 for 24 hours before addition of Calcein-AM labeled T cells. White bar represents untransfected control samples; black bars represent 2 ng/ml TGF-β1 treated siRNA transfected samples. Only HAS2 siRNA significantly inhibited TGF-β1 induced T cell adhesion (*, $p<0.05$, ***$p<0.001$ compared to untreated control; ###$p<0.001$ HAS2 siRNA compared to SC siRNA; ^, $P<0.05$, HAS1 siRNA versus HAS2 siRNA). Results are expressed as bound T cell number and are the mean±SEM (n=6) of one of three experiments.

FIG. 16A is a graph illustrating the effect of Pio and Rosi on TGF-β1 induced T cell adhesion to orbital fibroblasts. Confluent orbital fibroblasts were cultured in reduced serum for three days and exposed to 2 ng/ml TGF-β1 with or without different concentrations of Pio or Rosi for 24 hours. Peripheral T cell adhesion tests were performed as described previously. White bars represent vehicle; black bars represent 2 ng/ml TGF-β1. Both Pio and Rosi significantly inhibited TGF-β1 induced T cell adhesion (***$p<0.001$ compared to vehicle control; ###$p<0.001$ compared to TGF-β1). Results are expressed as bound T cell number and are the mean±SEM (n=6) of one of three experiments. FIG. 16B is a panel of images of confluent orbital fibroblast cultures in 8-chamber slides that were treated with 2 ng/ml TGF-β1, with or without 10 μM Pio or 10 μM Rosi for 24 hours. After the T cell adhesion assay, the cells were fixed and stained with 1 μg/ml Biotinylated HABP for HA (red, panels a, d, g), CD3 monoclonal antibody (green, panels b, e, f) and DAPI (blue). T cells appear on top of the fibroblasts, which are attached to the culture slide. Panels c, f, i: merged fluorescence with DAPI staining. Panels a, b, c: cells treated with TGF-β1; panels d, e, f: cells treated with TGF-β1+Pio; panels g, h, is cells treated with TGF-β1+Rosi.

DETAILED DESCRIPTION OF THE INVENTION

Figure 1A:
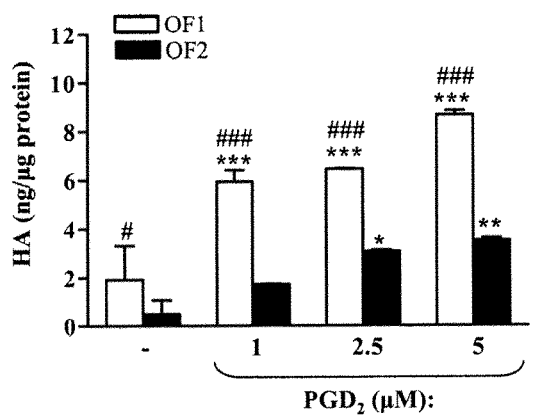
FIGS. 1A-C show that $PGD_2$ and $PGJ_2$ induce HA synthesis in human orbital fibroblasts. Confluent strains of human orbital fibroblasts (OF1 and OF2) were cultured in RPMI-1640 with 0.5% FBS for 3 days prior to treatment with $PGJ_2$, $PGD_2$ or vehicle (DMSO) for 18 hours. The cell culture media was assayed for HA by an HA ELISA as described in the accompanying examples. There was a significant increase in HA production by two strains of orbital fibroblasts following treatment with $PGD_2$ (1-5 μM) (FIG. 1A) and $PGJ_2$ (2 μM) (FIG. 1B). The experiment was performed in triplicate. *$p<0.05$, $p<0.01$, *$p<0.001$ compared to vehicle control; #$p<0.05$, ###$p<0.001$, OF1 versus OF2. Results are expressed as the mean±SD.

A first aspect of the invention relates to a method of treating thyroid eye disease. This method includes administering to a patient having thyroid eye disease an agent that interferes with hyaluronan synthesis in an amount that is effective to inhibit hyaluronan synthesis in a retro-ocular space.

As described below, in various embodiments of the present invention the agent(s) that interfere with HA synthesis do so via inhibiting the activity of the enzyme hyaluronan synthase, type 2 (HAS2) or interfering with DP1 signaling.

According to one embodiment, the agent that interferes with hyaluronan synthesis is RNAi that is specific for the enzyme HAS2.

An important feature of RNAi affected by siRNA is the double stranded nature of the RNA and the absence of large overhanging pieces of single stranded RNA, although dsRNA with small overhangs and with intervening loops of RNA has been shown to effect suppression of a target gene. In this specification, it will be understood that in this specification the terms siRNA and RNAi are interchangeable. Furthermore, as is well-known in this field RNAi technology may be effected by siRNA, miRNA or shRNA or other RNAi inducing agents. Although siRNA will be referred to in general in the specification. It will be understood that any other RNA inducing agent may be used, including shRNA, miRNA or an RNAi-inducing vector whose presence within a cell results in production of an siRNA or shRNA targeted to a target HAS2 transcript.

RNA interference is a multistep process and is generally activated by double-stranded RNA (dsRNA) that is homologous in sequence to the targeted HAS2 gene. Introduction of long dsRNA into the cells of organisms leads to the sequence-specific degradation of homologous gene transcripts. The long dsRNA molecules are metabolized to small (e.g., 21-23 nucleotide (nt)) interfering RNAs (siRNAs) by the action of an endogenous ribonuclease known as Dicer. The siRNA molecules bind to a protein complex, termed RNA-induced silencing complex (RISC), which contains a helicase activity and an endonuclease activity. The helicase activity unwinds the two strands of RNA molecules, allowing the antisense strand to bind to the targeted HAS2 RNA molecule. The endonuclease activity hydrolyzes the HAS2 RNA at the site where the antisense strand is bound. Therefore, RNAi is an antisense mechanism of action, as a single stranded (ssRNA) RNA molecule binds to the target HAS2 RNA molecule and recruits a ribonuclease that degrades the HAS2 RNA.

An "RNAi-inducing agent" or "RNAi molecule" is used in the invention and includes for example, siRNA, miRNA or shRNA targeted to a HAS2 transcript or an RNAi-inducing vector whose presence within a cell results in production of an siRNA or shRNA targeted to the target HAS2 transcript. Such siRNA or shRNA comprises a portion of RNA that is complementary to a region of the target HAS2 transcript. Essentially, the "RNAi-inducing agent" or "RNAi molecule" downregulates expression of the targeted HAS2 enzyme via RNA interference.

Preferably, siRNA, miRNA or shRNA targeting HAS2 enzyme are used.

Ideally, the method involves the systemic hydrodynamic delivery of the RNAi inducing agent, such as siRNA, miRNA or shRNA etc, to the subject. Non-hydrodynamic systemic delivery methods may also be used.

Other delivery methods suitable for the delivery of the RNAi inducing agent (including siRNA, shRNA and miRNA, etc) may also be used. For example, some delivery agents for the RNAi-inducing agents are selected from the following non-limiting group of cationic polymers, modified cationic polymers, peptide molecular transporters, lipids, liposomes and/or non-cationic polymers. Viral vector delivery systems may also be used. For example, an alternative delivery route includes the direct delivery of RNAi inducing agents (including siRNA, shRNA and miRNA) and even antisense RNA (asRNA) in gene constructs followed by the transformation of cells within the retro-ocular space with the resulting recombinant DNA molecules. This results in the transcription of the gene constructs encoding the RNAi inducing agent, such as siRNA, shRNA and miRNA, or even asRNA and provides for the transient and stable expression of the RNAi inducing agent in those transformed cells of the retro-ocular space. For example, such an alternative delivery route may involve the use of a lentiviral vector comprising a nucleotide sequence encoding a siRNA (or shRNA) which targets HAS2. Such a lentiviral vector may be comprised within a viral particle. Adeno-associated viruses (AAV) may also be used.

Exemplary RNAi specific for HAS2 include, without limitation, HAS2 RNAi available from Santa Cruz (e.g., sc-45329, sc-45329-SH), as well as the following sequences: 5'-UUGGAACCACACUCUUUGGd(TT)-3' (SEQ ID NO: 1) and 5'-CCAAAGAGUGUGGUUCCUUd(TT)-3' (SEQ ID NO: 2) (Sussmann et al., Circ. Res. 94:592-600 (2004), which is hereby incorporated by reference in its entirety.) Any other suitable RNAi molecules specific for HAS2 can also be used in accordance with the present invention.

According to a second embodiment, the agent that interferes with hyaluronan synthesis is a DP antagonist. The term "DP antagonist" (prostaglandin $D_2$ receptor antagonist or $PGD_2$ antagonist) means compounds that are capable of blocking, inhibiting, reducing or otherwise interrupting the interaction between prostaglandin $D_2$ and its receptor (e.g., DP receptor). The $PGD_2$ antagonist may be selective (interact preferentially with) for the DP1 receptor or may possess antagonistic effects at one or more other prostaglandin receptors.

Exemplary $PGD_2$ antagonists include, but are not limited to, compounds described as having $PGD_2$ antagonizing activity in PCT Published Applications WO97/00853, WO98/25919, WO01/79169, WO03/062200 WO01/66520, WO03/022814, WO03/078409, WO2004/103370, and WO02/094830; European Patent Applications EP945450, EP944614, and EP 1305286; and U.S. Application Publ. No. 20040220237, 20070244107, and 20080194600, all of which are hereby incorporated by reference in their entirety. Specific examples of $PGD_2$ antagonists include compounds L888839, MK0525, MK0524, BWA868C, laropiprant, S-555739, 2-[(1R)-9-(4-chlorobenzyl)-8-((R)-methylsulfinyl)-2,3,4,9-tetrahydro-1H-carbazol-1-yl]acetic acid, and 2-[(1R)-9-(4-chlorobenzyl)-8-((S)-methylsulfinyl)-2,3,4,9-tetrahydro-1H-carbazol-1-yl]acetic acid. Any other $PGD_2$ antagonists, whether now known or hereafter developed, can also be utilized in accordance with the present invention.

According to a third embodiment, the agent that interferes with hyaluronan synthesis is an agent that interferes with $PGD_2$ synthesis. Agents that interfere with $PGD_2$ synthesis include PGD synthase (PGDS) inhibitors. Suitable PGDS inhibitors include, without limitation, RNAi specific for PGDS (e.g., HSH007661 from GeneCopoeia, shRNA product NM_014485 from Sigma-Aldrich, and shRNA product TG315682 in pGFP-V-RS vector available from OriGene), and compounds as described in U.S. Patent Application Publ. No. 20080207651 and 20090221604, each of which is hereby incorporated by reference in its entirety. Exemplary PGDS include, without limitation, ethyl 3-(2-(3-fluorophenyl)pyrimidine-5-carboxamido)pyrrolidine-1-carboxylate, N-(1-(7,8-dihydro-5H-pyrano[4,3-d]pyrimidin-2-yl)pyrrolidin-3-yl)-2-(3-fluorophenyl)pyrimidine-5-carboxamide, 2-(3-fluorophenyl)-N-{1-[(methylamino)carbonyl]piperidin-4-yl}pyrimidine-5-carboxamide, 2-(3-fluorophenyl)-N-[1-(6-methyl-5,6,7,8-tetrahydropyrido[4,3-d]pyrimidin-2-yl)pyrrolidin-3-yl]pyrimidine-5-carboxamide, 2-(3-fluorophenyl)-N-[1-(2,2,2-trifluoroethyl)piperidin-4-yl] pyrimidine-5-carboxamide, 2-[4-(4-methoxyphenyl) piperazin-1-yl]-4-phenylthiazol-5-carboxylic acid, (E)-3-{2-[4-(4-methoxyphenyl)piperazin-1-yl]-4-phenylthiazol-5-yl}acrylic acid, 3-{2-[4-(4-methoxyphenyl)piperazin-1-yl]-4-phenylthiazol-5-yl}propionic acid, [4-phenyl-2-(4-phenylpiperazin-1-yl)thiazole-5-yl]acetic acid, {2-[4-(2-methoxyphenyl)piperazine-1-yl]-4-phenylthiazol-5-yl}acetic acid, [2-(4-benzylpiperazin-1-yl)-4-phenylthiazol-5-yl]acetic acid, N-{2-[4-phenyl-2-(4-phenylpiperazin-1-yl) thiazol-5-yl]acetyl}methanesulphonamide, N-(3-{2-[4-(4-methoxyphenyl)piperazin-1-yl]-4-phenylthiazol-5-yl}propionyl)-benzenesulphonamide, N-(2-{2-[4-(4-methoxyphenyl)piperazine-1-yl]-4-phenylthiazol-5-yl}acetyl)-benzenesulphonamide, N-{2-[4-phenyl-2-(4-phenylpiperazin-1-yl)thiazole-5-yl] acetyl}benzenesulphonamide, 4-phenyl-2-(4-phenylpiperidin-1-yl)thiazole-5-carboxylic acid, 2-[4-(2-methoxyphenyl)piperazine-1-yl]-4-phenylthiazole-5-carboxylic acid, 1-(4-methoxyphenyl)-4-[4-phenyl-5-(1H-tetrazol-5-yl)thiazol-2-yl]piperazine, {2-[4-(4-methoxyphenyl)piperazine-1-yl]-4-phenylthiazol-5-yl}acetic acid, or a pharmaceutically acceptable salt or solvate thereof. Any other PGDS inhibitors, whether now known or hereafter developed, can also be utilized in accordance with the present invention.

According to a fourth embodiment, the agent that interferes with hyaluronan synthesis is 15d-PGJ2, a homolog thereof, or a pro-drug that is metabolized to form 15d-PGJ2 upon administration.

According to a fifth embodiment, the agent that interferes with hyaluronan synthesis is a PPARγ agonist. Exemplary PPARγ agonists include, without limitation, cyclopentenone class prostaglandins such as the native PPARγ agonist 15-deoxy-Δ12,14-Prostaglandin J2, members of the thiazolidinedione class of PPARγ agonists such as the glitazones, lysophosphatidic acid ("LPA") or LPA derivatives (McIntyre et al., *Proc. Natl. Acad. Sci. USA* 100:131-136 (2003), which is hereby incorporated by reference in its entirety), members of the tyrosine-based class of PPARγ agonists, members of the indole-derived class of PPARγ agonists, and combinations thereof. Preferred thiazolidinediones and/or glitazones include, without limitation, ciglitazone, troglitazone, pioglitazone, rosiglitazone, SB213068 (Smith Kline Beecham), GW1929, GW7845 (Glaxo-Wellcome), and L-796449 (Merck). Suitable tyrosine-based agonists include N-(2-benzylphenyl)-L-tyrosine compounds (Henke et al., *J. Med. Chem.* 41:5020-5036 (1998), which is hereby incorporated by reference in its entirety. Suitable indole-derived agonists include those disclosed, e.g., in Hanks, et al., *Biorg. Med. Chem LLH* 9(23):3329-3334 (1999), which is hereby incorporated by reference in its entirety. Any other PPARγ agonists, whether now known or hereafter developed, can also be utilized in accordance with the present invention.

From the foregoing description, it is intended in certain embodiments that the agent that interferes with hyaluronan synthesis is not a PPARγ agonist. In other embodiments, the agent that interferes with hyaluronan synthesis is one or more agents other than a PPARγ agonist, optionally in combination with one or more PPARγ agonists.

According to a sixth embodiment, a combination of any two or more of the HAS2-specific RNAi agent, the PGDS, the DP antagonist, and the PPARγ agonist can be administered together (in a single formulation) or concurrently (in separate formulations).

The agent(s) that interferes with hyaluronan synthesis can be administered using any suitable mode of delivery that is effective for delivery the agent to the retro-ocular space, which is the site where excessive hyaluronan synthesis occurs in thyroid eye disease.

Exemplary modes of administration include, without limitation, orally, by inhalation, by intranasal or airway instillation, optically, intranasally, topically, transdermally, parenterally, subcutaneously, intravenous injection, intra-arterial injection, injection to the retro-ocular space, intradermal injection, intramuscular injection, intrapleural instillation, intraperitoneally injection, intraventricularly, intralesionally, by application to mucous membranes, or implantation of a sustained release vehicle.

The above-identified agents are preferably administered in the form of pharmaceutical formulation that includes one or more of the active agents, alone or in combination with one or more additional active agents, together with a pharmaceutically acceptable carrier. The term "pharmaceutically acceptable carrier" refers to any suitable adjuvants, carriers, excipients, or stabilizers, and can be in solid or liquid form such as, tablets, capsules, powders, solutions, suspensions, or emulsions. The carrier is a preferably suitable for ophthalmic delivery.

Typically, the composition will contain from about 0.01 to 99 percent, preferably from about 20 to 75 percent of active agents, together with the adjuvants, carriers and/or excipients.

One exemplary formulation is a solid composition containing one or more agents that interfere with hyaluronan synthesis and a mucoadhesive substance in the conjunctival sac, wherein the adhesion strength of the mucoadhesive substance is in the range of from 200 to 1000 g. The use of such mucoadhesive substance for posterior optical drug delivery is described in U.S. Patent Application Publ. No. 20090036552, which is hereby incorporated by reference in its entirety.

Another exemplary formulation is an injectable sustained-release formulation that includes one or more agents that interfere with hyaluronan synthesis and a nanosphere. The nanosphere contains a particle that comprises a particle-forming component capable of forming a vesicle, and an agent-carrying component capable of forming a complex with the therapeutic agent(s) via electrostatic charge-charge interaction or hydrophobic-hydrophobic interaction. The particle-forming component has at least one head group moiety selected from a hydrophobic head group moiety, a polar head group moiety and a combination thereof. The agent-carrying component is a chemical entity that contains one or more negatively or positively charged groups. The use of such a nanosphere composition is described in U.S. Patent Application Publ. No. 20080118500, which is hereby incorporated by reference in its entirety.

Tablets, capsules, and the like can also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it can contain, in addition to materials of the above type, a liquid carrier such as a fatty oil.

Various other materials may be present as coatings or to modify the physical form of the dosage unit. For instance, tablets can be coated with shellac, sugar, or both. A syrup can contain, in addition to active ingredient, sucrose as a sweetening agent, methyl and propylparabens as preservatives, a dye, and flavoring such as cherry or orange flavor.

The active agent(s) may also be administered in injectable dosages by solution or suspension of these materials in a physiologically acceptable diluent with a pharmaceutical adjuvant, carrier or excipient. Such adjuvants, carriers and/or excipients include, but are not limited to, sterile liquids, such as water and oils, with or without the addition of a surfactant and other pharmaceutically and physiologically acceptable components. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

These active compounds may also be administered parenterally. Solutions or suspensions of these active compounds can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Transdermal formulations include, without limitation, a transdermal delivery system, typically in the form of a patch that contains a depot of the active drug(s) in a pharmaceutically acceptable transdermal carrier, or simply a solution phase carrier that is deposited onto the skin, where it is absorbed. A number of transdermal delivery systems are known in the art, such as U.S. Pat. No. 6,149,935 to Chiang et al., PCT Application Publ. No. WO2006091297 to Mitragotri et al., EP Patent Application EP1674068 to Reed et al., PCT Application Publ. No. WO2006044206 to Kanios et al., PCT Application Publ. No. WO2006015299 to Santini et al., each of which is hereby incorporated by reference in its entirety.

According to a further embodiment, which is suitable for implantation, the pharmaceutical formulation may be in the form of a polymeric matrix in which the agents to be administered are captured. Release of the agents can be controlled via selection of materials and the amount of drug loaded into the vehicle. Implantable drug delivery systems include, without limitation, microspheres, hydrogels, polymeric reservoirs, cholesterol matrices, polymeric systems, and non-polymeric systems. A number of suitable implantable delivery systems are known in the art, such as U.S. Pat. No. 6,464,687 to Ishikawa et al., U.S. Pat. No. 6,074,673 to Guillen, each of which is hereby incorporated by reference in its entirety.

Preferred dosages of the above-identified agents are between about 0.001 to about 2 mg/kg, preferably 0.05 to about 1 mg/kg, most preferably about 0.05 to about 0.5 mg/kg. Administration of the agents can be repeated as needed, e.g., up to several times daily during treatment of TED and according to a periodic schedule (once weekly or up to several times a week, including once daily) to inhibit recurrence of thyroid eye disease.

The above-identified therapeutic treatments can also be used in combination with one or more current therapies, including without limitation, radiation therapy, prednisone therapy, and surgical decompression.

The patients to be treated in accordance with the present invention can have varying degrees of severity of TED. Consequently, it is expected that the degree of symptom control can constitute preventing further development of TED symptoms or a reduction in the severity of TED symptoms.

In certain embodiments, patients having TED can be those that have no other medical conditions, such as diabetes. In other embodiments, patients having TED can also be type 2 diabetic and receiving concurrent treatment for their diabetes, including treatment with a PPARγ agonist such as one of the above-identified thiazolidinediones (e.g., pioglitazone or rosiglitazone).

EXAMPLES

The following examples are provided to illustrate embodiments of the present invention but they are by no means intended to limit its scope.

Materials & Methods for Examples 1-7

Reagents $PGD_2$, $PGJ_2$, MK0524, Ramatroban (BAY-u3405), BW 245C, 4-benzhydryloxy-1-[3-(1H-tetrazol-5-yl)-propyl]-piperidine (HQL-79), 13,14-dihydro-15-keto-PGD2 (DK-$PGD_2$); anti-DP1, anti-H-PGDS, anti-Cox-1, anti-Cox-2 antibodies were purchased from Cayman Chemical (Ann Arbor, Mich.). Forskolin, A23187 and isobutylmethyl-xanthine (IBMX) were purchased from Sigma (St. Louis, Mo.). Anti-DP2 antibody was purchased from R&D system (Minneapolis, Minn.). All the drugs were dissolved in DMSO.

Tissue Collection and Cell Culture

Orbital fibroblasts: Primary orbital fibroblasts were isolated from TED patients undergoing orbital decompression surgery. The protocols for orbital biopsy and blood sample, described below, were approved by the Internal Review Board and informed, written consent was obtained from all patients. The primary fibroblasts were established by standard explant techniques (Smith et al., *J Clin Endocrinol Metab* 80(9):2620-2625 (1995); Baglole et al., *Methods Mol Med* 117:115-127 (2005), each of which is hereby incorporated by reference in its entirety) and cultured in RPMI 1640 supplemented with 10% fetal bovine serum (FBS) (Hyclone, Logan Utah), 2-mercaptoethanol (Eastman Kodak, Rochester, N.Y.), L-glutamine (Life Technologies, Grand Island, N.Y.), HEPES (US Biochemical Corp., Cleveland, Ohio), nonessential amino acids, sodium pyruvate, and gentamicin (Life Technologies). Fibroblasts were characterized by their adherent morphology, expression of vimentin and types I and III collagen and absence of CD45, factor VIII or cytokeratin. Fibroblasts were used at the earliest passage possible (between passages 4 to 10). Human T cells: Lymphocytes were isolated from 60 ml of peripheral blood obtained during orbital decompression surgery. Whole blood was separated over a Ficoll-Paque Plus Gradient (Amersham Biosciences, Piscataway, N.J.) to obtain peripheral blood mononuclear cells. T cells were enriched using CD3/CD28 T cell Expander beads (Invitogen). Specifically, $5\times10^6$ lymphocytes were incubated with CD3/CD28 beads at a ratio 1:1 in RPMI 1640 with 10% FBS media at 37° C. for 2 days. After that, 50 U/ml of recombinant interleukin-2 (rIL-2) was added to the culture and incubated for another 2-3 days. On day 5, cells were diluted to a concentration of $0.5\times10^6$ cells/ml in medium containing 50 U/ml rIL-2 and incubated for an additional 3-7 days. Cellular purity was assessed using an anti-CD3-PE antibody (BD Biosciences, San Jose, Calif.) and analyzed on a FACSCalibur flow cytometer (BD Biosciences). The T-cell purity was >95%.

Co-Culture of Mast Cells with Orbital Fibroblasts

HMC-1 mast cells were allowed to proliferate in Iscove's Modified Dulbecco's Medium (IMDM) enriched with 5% FBS. Co-cultures were initiated by introducing HMC-1 cells to confluent cultures of fibroblasts as previously described (24). Mast cells were washed with RPMI-1640 medium (0.5% FBS) once before addition to the fibroblasts (1:1 ratio, unless otherwise specified). After 4 hours, the media and HMC-1 cells were removed by gently rinsing in PBS and fresh RPMI-1640 medium (0.5% FBS) was used to cover the cells. Alternatively, fibroblasts and mast cells were co-cultured in a transwell system (0.4 µm; Greiner Bio-one, New York, N.Y.) with fibroblasts being cultured on the bottom and the mast cells in the top chamber. The ratio of mast cells to fibroblasts was varied from 5:1 to 20:1.

Quantitation of HA

Aliquots of culture medium were removed at indicated time points, centrifuged (5 min, 8,000×g at 4° C.) and HA levels quantified by enzyme-linked immunosorbent assay (ELISA) according to the manufacturer's protocol (R&D Systems). Briefly, samples were incubated in HA-binding protein (HABP)-coated microwells, allowing HA in samples to react with the immobilized HABP. After the removal of unbound molecules by washing, biotinylated-HABP was added to the microwells. Following a second wash, strepta-vidin-conjugated to horseradish peroxidase was added. After the last wash, the chromogenic substrate was added and HA levels were determined using a Varioskan Flash plate reader (Thermo Fisher Scientific, Milford, Mass.).

Agarose Gel Electrophoresis of HA

Fibroblasts were cultured to confluence in 10 cm² dishes in RPMI containing 10% FBS, followed by RPMI with 2% FBS for 3 days. Fibroblasts were then treated with 5 µM $PGD_2$ or control (DMSO) for 18 hours. Cell culture supernatant was centrifuged (5 min at 8,000×g at 4° C.) and half of the sample digested with 1 TRU/ml *Streptomyces* hyaluronidase (Sigma) at 37° C. for 4 hours; the remainder of the sample was mock-digested. Following digestion with proteinase K (120 µg/ml) (Qiagen, Valencia, Calif.) at 37° C. for 4 hours, the samples were concentrated using Vivaspin 10,000 Da cut-off ultrafiltration spin column (Sartorius Stedim Biotech, Goettingen, Germany), washed with PBS and analyzed by 1% agarose electrophoresis. Select-HA HiLadder (Hyalose LLC, Oklahoma City, Okla.) and blue dextran (Sigma; molecular weight $2\times10^6$ Da) were also run as standards. The gel was stained with 0.005% Stains-All (Sigma) in 50% ethanol overnight at room temperature before being scanned on an HP scanner.

Western Blotting

Following treatments, cells were lysed in 1×SDS sample buffer and protein concentrations determined using the DC protein assay kit (Bio-Rad, Hercules, Calif.). Samples were separated on a 9% or 12% SDS-PAGE gel, transferred to polyvinylidene difluoride (PVDF) membranes, and subjected to immunoblotting with antibodies against DP1 (1:1,000), DP2 (1:500), H-PGDS (1:500), Cox-1 (1:500), or Cox-2 (1:500). As a loading control, membranes were re-probed for GAPDH (1:3000, Calbiochem, San Diego, Calif.).

Measurement of cAMP cAMP levels were quantified using a time-resolved fluorescence resonance energy transfer (TR-FRET) immunoassay from Perkin Elmer (Waltham, Mass.) according to the manufacturer's protocol. Briefly, orbital fibroblasts were detached with a non-enzymatic cell dissociation solution (Versene, Invitrogen) and re-suspended in Stimulation Buffer (pH 7.4; 1×HBSS buffer containing 5 mmol/L HEPES buffer and 0.01%-0.1% BSA) containing 0.5 mM IBMX and labeled with the Alexa Fluor® 647-labeled anti-cAMP antibody. Finally, the cells were incubated with drugs at the indicated times. Following addition of the detection buffer, the amount of cAMP signal was measured.

Measurement of $PGD_2$

HMC-1 cells ($1\times10^6$/well) were seeded into 6-well plates and cultured in IMDM medium with 5% FBS in the absence or presence of HQL-79 (H-PGDS inhibitor, 100 µM) at 37° C. for 60 minutes. The cells were then washed and resuspended in RPMI 1640 medium with 0.5% FBS. After 2 hours incubation, the cells were stimulated with 10 µM calcium ionophore A23187 for 30 minutes. The culture media were collected and $PGD_2$ in the supernatants was quantified by $PGD_2$-MOX EIA kits (Cayman Chemical).

Reverse Transcriptase PCR (RT-PCR) and Quantitative RT-PCR (qRT-PCR)

RNA was isolated from orbital fibroblasts or T cells using an RNeasy Mini kit (Qiagen). RNA was reverse transcribed to cDNA using iScript cDNA synthesis kit (Bio-Rad) and diluted 5-fold in RNase-free $H_2O$. Forward and reverse primers for each gene are shown in Table I. RT-PCR: The PCR reaction was performed using Qiagen Fast Cycling PCR kit for 30 cycles in a Bio-Rad thermal cycler. The PCR product was visualized on a 5% acrylamide gel stained with ethidium bromide. Amplifications without reverse transcriptase were carried out as negative controls. qRT-PCR: qRT-PCR was performed in a Bio-Rad iCycler containing B-R SYBR Green SuperMix for IQ (Quanta Biosciences, Gaithersburg, Md.). Efficiency of the amplification was determined to be >90%.

TABLE I

| Gene | Primer Sequence | Size |
| --- | --- | --- |
| Has1 (NM-001523) | Forward 5'-TGTGTATCCTGCATCAGCGGT-3' (SEQ ID NO: 7) Reverse 5'-CTGGAGGTGTACTTGGTAGCATAACC-3' (SEQ ID NO: 8) | 172 bP |

TABLE I-continued

| Gene | Primer Sequence | Size |
|---|---|---|
| HAS2 (NM-005328) | Forward 5'-GCCTCATCTGTGGAGATGGT-3' (SEQ ID NO: 9)<br>Reverse 5'-ATGCACTGAACACACCCAAA-3' (SEQ ID NO: 10) | 181 bP |
| HAS3 (NM-005329) | Forward 5'-GGCATTATCAAGGCCACCTA-3' (SEQ ID NO: 11)<br>Reverse 5'- AGGCCAATGAAGTTCACCAC-3' (SEQ ID NO: 12) | 184 bP |
| DP1 (NM-000953) | Forward 5'-TCTGCGCGCTACCTTTCATG-3' (SEQ ID NO: 13)<br>Reverse 5'-TCCTCGTGGACCATCTGGATA-3' (SEQ ID NO: 14) | 84 bP |
| DP2 (NM-004778) | Forward 5'-TTTCTCAACATGTTCGCCAG-3' (SEQ ID NO: 15)<br>Reverse 5'-AAGCACCAGGCAGACTTTGT-3' (SEQ ID NO: 16) | 131 bP |
| 7S RNA (NR-002715) | Forward 5'-ACCACCAGGTTGCCTAAGGA-3' (SEQ ID NO: 17)<br>Reverse 5'-CACGGGAGTTTTGACCTGCT-3' (SEQ ID NO: 18) | 68 bP |

Amplification of 7S ribosomal RNA was carried out for each cDNA (in triplicate) for normalization. Threshold cycle number (CO of amplification in each sample was determined by Bio-Rad software and the relative mRNA abundance was calculated as the $C_t$ for amplification of a gene-specific cDNA minus average $C_t$ for 7S, expressed as a power of 2; i.e., $2^{\Delta Ct}$.

Gene Knockdown Using siRNA

Orbital fibroblasts were cultured to 80-90% confluence and transfected with 80 nM of HAS1, HAS2 or scrambled control (SC) siRNA (Santa Cruz) using Lipofectamine 2000 (Invitrogen). Forty eight hours post-transfection, RPMI containing 0.5% FBS was added. Twenty-four hours later, the cells were treated with or without 5 μM $PGD_2$ for 2 hours (for qRT-PCR analysis) or 18 hours (for analysis of HA secretion).

Statistical Analysis

Statistical analysis was performed using GraphPad Prism (GraphPad Software, Inc, La Jolla, Calif.). For comparison between groups of three or more, an analysis of variance (ANOVA) with Newman-Keuls multiple comparison test was used to determine differences between treatments. Error bars represent the standard deviation from the mean of triplicate samples. A p value of less than 0.05 is considered significant. All experiments were performed at least three times.

Figure 1B:
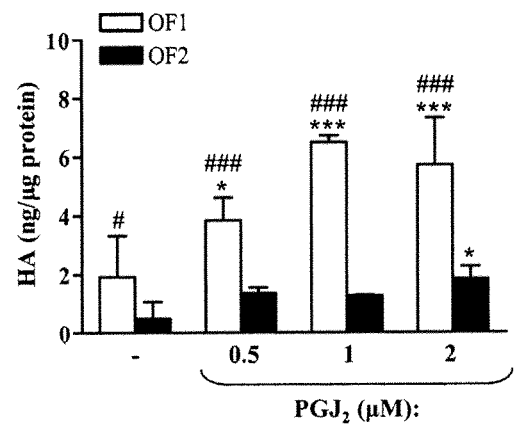

Example 1—D and J Series Prostaglandins Induce HA Synthesis by Human Orbital Fibroblasts It was previously reported that $PGD_2$ and $PGJ_2$ induce adipogenesis in human orbital fibroblasts (Feldon et al., Am J Pathol 169(4):1183-1193 (2006), which is hereby incorporated by reference in its entirety). Here, it was examined whether $PGD_2$ or $PGJ_2$ would also induce HA production. Two strains of human orbital fibroblasts (OF1 and OF2) from two different TED patients were treated with increasing concentrations of $PGD_2$ or $PGJ_2$ for 18 hours, and HA levels were detected in the cell culture supernatant by a commercial HA ELISA. FIG. 1A shows that basal levels of HA differed significantly between the two orbital fibroblast strains (OF1: 1.9±1.4 ng/μg protein versus OF2: 0.5±0.6 ng/μg protein; #p<0.05). Treatment of the fibroblast strain designated OF1 with either $PGJ_2$ or $PGD_2$ resulted in significantly more HA production compared to OF2. $PGD_2$ and $PGJ_2$ also significantly increased HA synthesis by both fibroblast strains in a dose-dependant manner, with 5 μM $PGD_2$ and 2 μM $PGJ_2$ yielding the largest induction (FIGS. 1A-B). Higher concentrations of $PGD_2$ nor $PGJ_2$ did not result in a further increase in HA synthesis in either of the two fibroblast strains. Therefore, most of the remaining experiments were conducted using 5 μM $PGD_2$ or 2 μM $PGJ_2$.

Figure 1C:
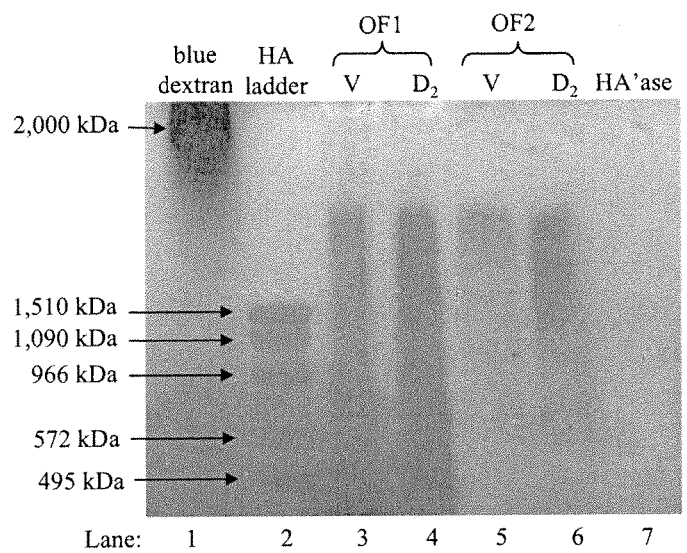

Agarose gel electrophoresis was performed to analyze the molecular size(s) of HA produced by the orbital fibroblasts. HA is an extremely high molecular weight polysaccharide (approximately $10^5$-$4\times10^6$ Da) and can be separated from other GAGs by ultrafiltration combined with agarose gel electrophoresis (Lee et al., Anal Biochem 219(2):278-287 (1994), which is hereby incorporated by reference in its entirety). FIG. 1C confirms the presence of HA in the cell culture media of two fibroblast strains (OF1 and OF2) (lanes 3-6). Treatment with $PGD_2$ ($D_2$) increased HA compared with vehicle (V) (Lanes 4 and 6 compared with Lanes 3 and 5). OF1 also produces relatively more low molecular weight (MW) HA compared to OF2. Streptomyces hyaluronidase was used to digest the HA in the samples. Unlike other hyaluronidases, this enzyme is specific for hyaluronic acid and is inactive with chondroitin and chondroitin sulfate (Ohya et al., Biochim Biophys Acta 198(3):607-609 (1970), which is hereby incorporated by reference in its entirety). The Streptomyces hyaluronidase-digested sample (HA'ase, lane 7) did not show any staining, confirming the HA specificity of the assay. Together, these results demonstrate that orbital fibroblasts increase the production of HA when exposed to $PGD_2$.

Figure 2:
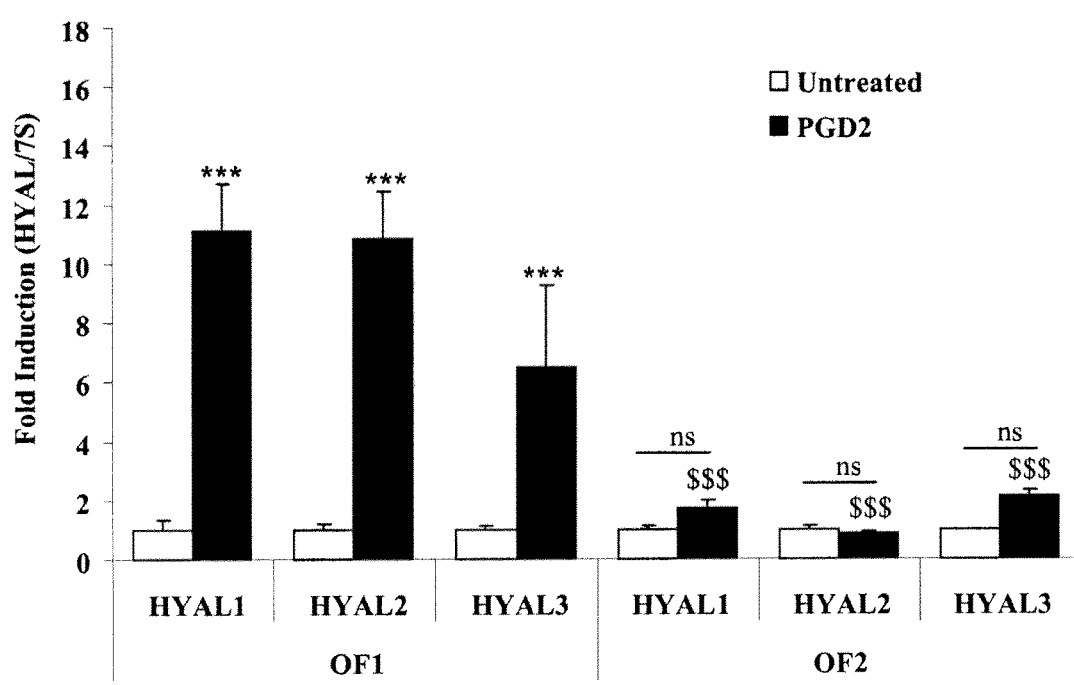
FIG. 2 is a graph illustrating the differential induction in hyaluronidase mRNA between two orbital fibroblast strains. cDNA from orbital fibroblast strains OF1 and OF2 treated with 5 μM $PGD_2$ or vehicle (Untreated) for 4 hours was assessed by qRT-PCR. There was a significant increase in mRNA expression for all three hyaluronidase isoforms (HYAL1, HYAL2 and HYAL3) when OF1 was treated with 5 μM $PGD_2$ (***$p<0.0001$, compared to Untreated). There was no significant increase in HYAL1-3 in $PGD_2$-treated OF2 cells (ns, compared to Untreated). The induction of HYAL1, HYAL2 and HYAL3 mRNA in $PGD_2$-treated OF1 was significantly higher than $PGD_2$-exposed OF2 HYAL expression (\$\$\$$p<0.0001$, for each respective HYAL). Results are expressed as the mean±SD (n=3).

Example 2—Differential Expression of $PGD_2$-Induced Hyaluronidase in Two Orbital Fibroblast Strains Hyaluronidases (HYAL1-3) depolymerize HA into low MW polymers (Noble, Matrix Biol 21(1):25-29 (2002), which is hereby incorporated by reference in its entirety). To determine if the apparent increase in low MW HA in PGD$_2$-treated OF1 fibroblast strain might be the result of increased hyaluronidase expression, OF1 and OF2 were treated with 5 µM PGD$_2$ and hyaluronidase mRNA levels were assessed. There was a significant induction in HYAL1, HYAL2 and HYAL3 mRNA following treatment of OF1 with PGD$_2$ (FIG. 2). In contrast, OF2 failed to significantly increase hyaluronidase mRNA expression. The induction in hyaluronidases in OF1 caused by PGD$_2$ was significantly greater than PGD$_2$-treated OF2 HYAL mRNA levels (FIG. 2). These results are the first to demonstrate regulation of hyaluronidase mRNA by PGD$_2$ in human orbital fibroblasts.

Figure 3A:
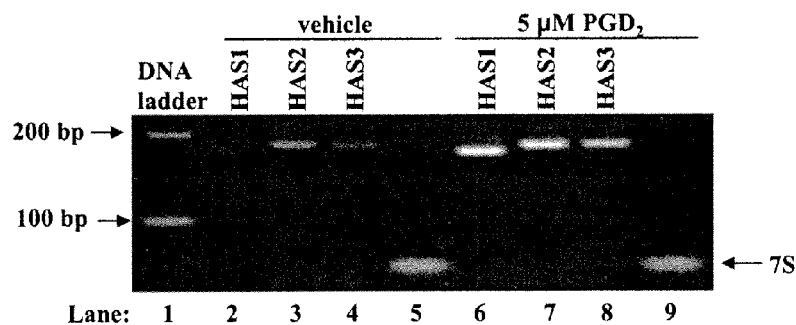
FIGS. 3A-D illustrate the induction of HAS mRNA expression by $PGD_2$ in human orbital fibroblasts.
Figure 3B:
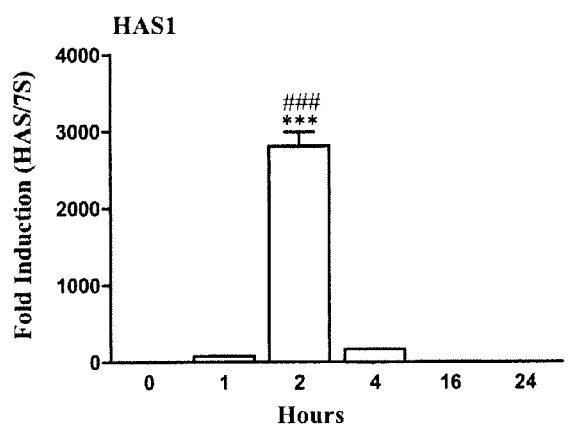
Figure 3C:
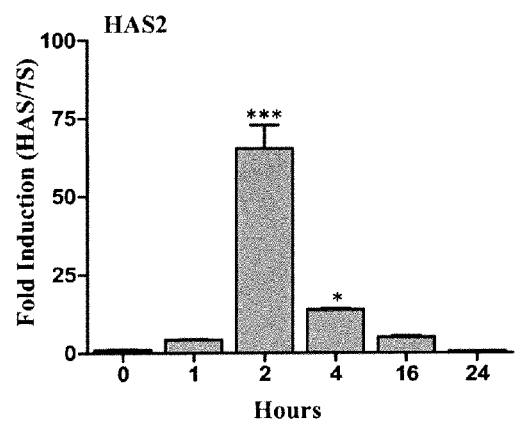
Figure 3D:
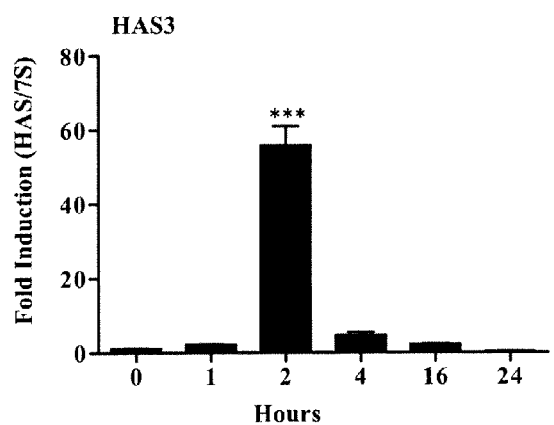

Example 3—PGD$_2$ Induces Hyaluronan Synthase mRNA Expression in Human Orbital Fibroblasts The effect of PGD$_2$ on HAS mRNA expression also was assessed. FIG. 3A shows that all three HAS genes are expressed in orbital fibroblasts. In untreated cells (vehicle), HAS1 mRNA is very low and scarcely detectable. In contrast, HAS2 and HAS3 mRNA is relatively greater. Following 2 hours of PGD$_2$ treatment, the mRNA for all three HAS isoforms increased significantly (FIG. 3A-D), with HAS1 exhibiting the greatest induction. The increase in HAS1 at two hours was significantly greater compared to either HAS2 or HAS3 (compare FIG. 3B with FIGS. 3C-D; ###p<0.001). The mRNA for all three HAS isoforms declined rapidly, and by 16 hours there was no significant difference compared to untreated (0 Hours). 7S ribosomal mRNA expression remained the same, regardless of treatment (FIG. 3A, compare lanes 5 and 9) and was used to normalize the qRT-PCR results (FIGS. 3B-D).

Figure 4A:
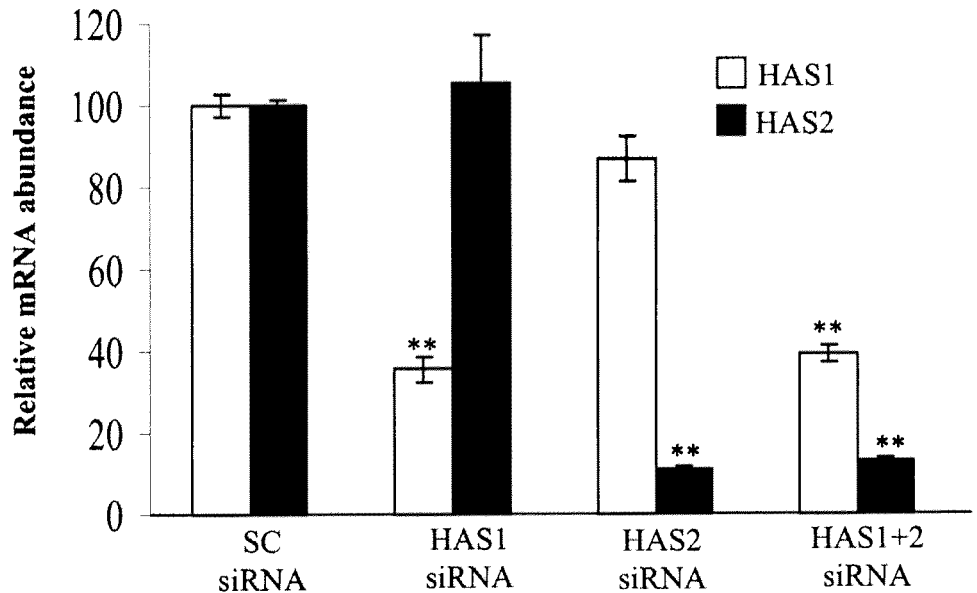
FIGS. 4A-B are graphs illustrating that $PGD_2$-induced HA production by orbital fibroblasts is dependent on HAS2 expression. For FIG. 4A, orbital fibroblasts were transfected with siRNA for HAS1, HAS2, or a combination as described in the accompanying Examples. The cells were cultured for 24 hours in RPMI-1640 with 0.5% FBS, treated with 5 μM $PGD_2$ for 2 hours and HAS gene levels were analyzed by qRT-PCR. The mRNA for HAS1 and HAS2 in the $PGD_2$-treated SC siRNA samples was standardized to 100 for comparison of gene expression. Each siRNA reduced its target mRNA expression selectively and significantly (up to 80%). **$p<0.01$. For FIG. 4B, orbital fibroblasts transfected with siRNA for HAS1, HAS2 or a combination, were cultured in RPMI-1640 with 0.5% FBS for 24 hour, and then exposed to 5 μM $PGD_2$ for 18 hours and HA was analyzed by HA-ELISA. Fibroblasts treated with $PGD_2$ (black bars) increased HA synthesis. Knock-down of HAS2, but not HAS1, significantly reduced the ability of $PGD_2$ to induce HA in human orbital fibroblasts. *$p<0.05$; **$p<0.01$ compared to $PGD_2$-treated SC siRNA-transfected; ##$p<0.01$ untreated SC siRNA versus untreated HAS2 siRNA; ns, no significance, HAS2 siRNA transfected, $PGD_2$-treated fibroblasts versus untreated SC-siRNA-transfected cells.

Example 4—PGD$_2$-Induced HA Production by Orbital Fibroblasts is Dependent on HAS2 Expression To verify whether or not HA synthesis was directly related to HAS expression, siRNA was used to selectively knockdown HAS1 or HAS2 mRNA levels in fibroblasts that were treated with PGD$_2$. FIG. 4A shows that siRNA directed against HAS1 or HAS2 selectively and significantly reduced (by approximately 75%-80% of mRNA levels) PGD$_2$-induced HAS1 (open bars) and HAS2 (black bars), compared to the scrambled siRNA (SC siRNA).

Figure 4B:
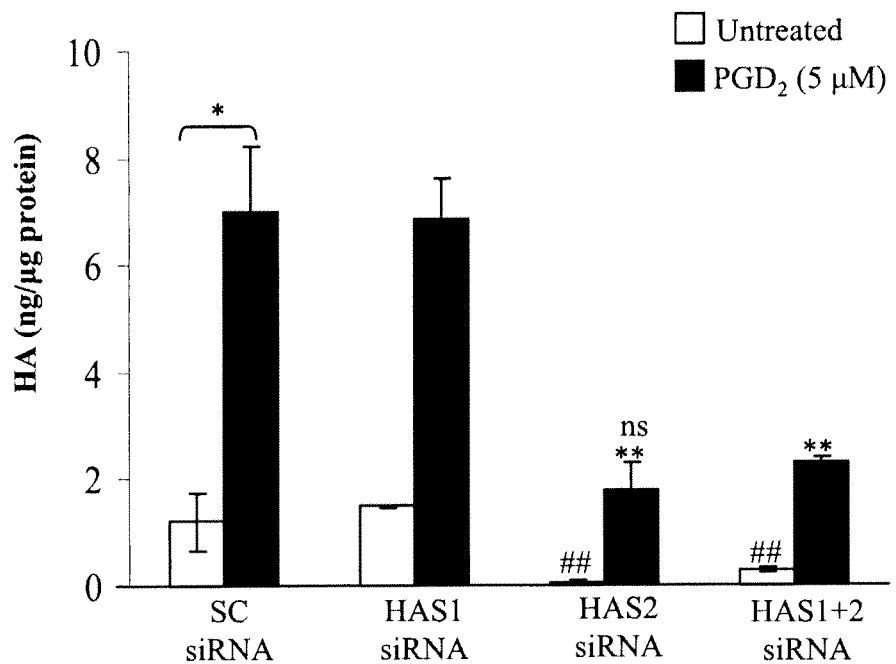

Orbital fibroblasts that were untreated (open bars) or treated with PGD$_2$ (black bars) were then analyzed for HA after transfection with siRNA against HAS1 and/or HAS2 (FIG. 4B). Those fibroblasts transfected with the SC siRNA exhibited a significant increase in HA synthesis in response to PGD$_2$ (FIG. 4B, compared with FIG. 1A). Despite the significant increase in HAS1 mRNA induced by PGD$_2$ (FIG. 3A-B), attenuation of HAS1 expression did not block PGD$_2$-induced HA production (FIG. 4B). In contrast, reduction in HAS2 mRNA expression significantly reduced both untreated and PGD$_2$-induced HA production when compared to the SC siRNA control (FIG. 4B). This reduction in HA synthesis in the HAS2 siRNA transfected, PGD$_2$-treated fibroblasts was not significantly different compared to untreated SC-siRNA-transfected cells (ns, p=0.13). These data support that HAS2 is the dominant isoform responsible for the increased HA synthesis by orbital fibroblasts in response to PGD$_2$.

Figure 5A:
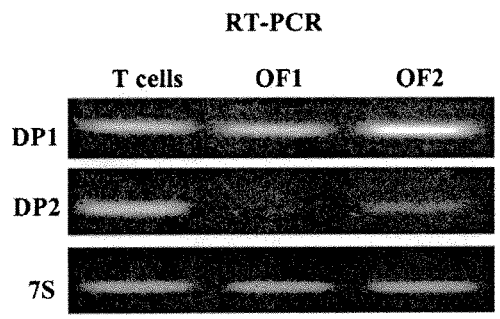
FIGS. 5A-G illustrate the ability of $PGD_2$ and $PGJ_2$ to induce HA production in human orbital fibroblasts via DP1, but not DP2, activation.
Figure 5B:
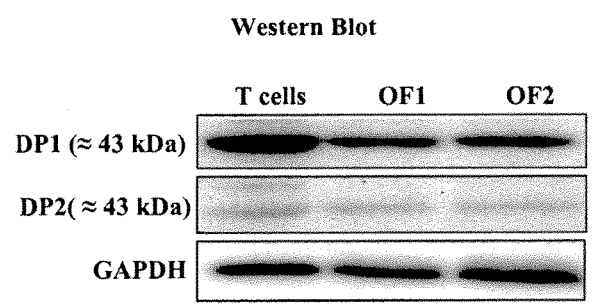

Example 5—PGD$_2$ and PGJ$_2$ Induce HA Production in Human Orbital Fibroblasts Via DP1, but not DP2, Activation Both PGD$_2$ and PGJ$_2$ can exert their biological functions via activation of DP1 or DP2 (Pettipher et al., *Nat Rev Drug Discov* 6(4):313-325 (2007), which is hereby incorporated by reference in its entirety). It was therefore examined whether or not human orbital fibroblasts express DP receptors. RT-PCR and western blot analysis revealed that orbital fibroblasts (OF1 and OF2) express both DP1 and DP2 mRNA and protein, respectively (FIGS. 5A-B). Protein expression of DP1 and DP2 in orbital fibroblasts was comparable to that of human T cells, which are well-known to express DP receptors, particularly DP2 (Nagata et al., *FEBS Lett* 459(2):195-199 (1999); Nagata et al., *Prostaglandins Leukot Essent Fatty Acids* 69(2-3):169-177 (2003), each of which is hereby incorporated by reference in its entirety). Both orbital fibroblast strains (OF1 and OF2) expressed considerably more DP1 mRNA and protein compared to DP2 (FIGS. 5A-B).

Figure 5C:
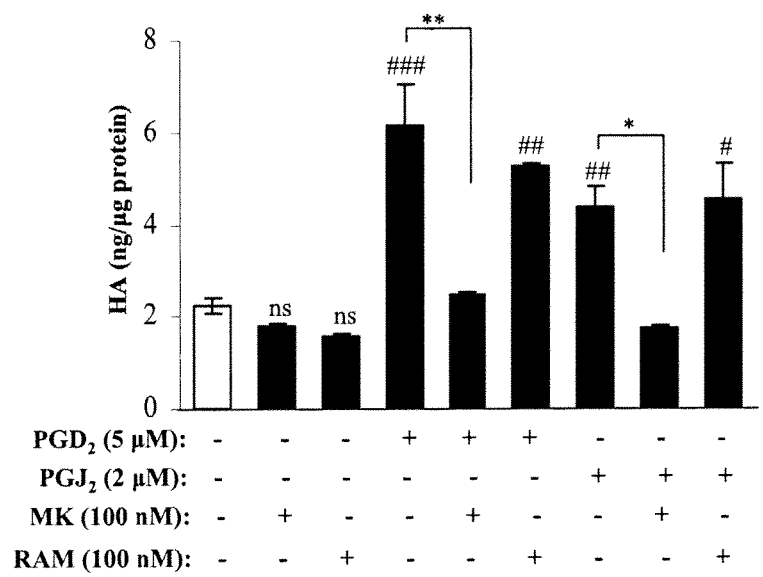

To determine which DP was involved in the PGD$_2$-mediated induction of HA, well-described selective pharmacological antagonists directed against either DP1 (MK-0524) (Sturino et al., *J Med Chem* 50(4):794-806 (2007); Leblanc et al., *Bioorg Med Chem Lett* 19(8):2125-2128 (2009), each of which is hereby incorporated by reference in its entirety) or DP2 (Ramatroban) (Pettipher et al., *Nat Rev Drug Discov* 6(4):313-325 (2007); Royer et al., *Eur J Clin Invest* 38(9):663-671 (2008), each of which is hereby incorporated by reference in its entirety) were utilized. Fibroblasts were untreated or were pretreated with either MK-0524 or Ramatroban for 1 hour with or without PGD$_2$ or PGJ$_2$. FIG. 5C shows neither MK-0524 (MK) nor Ramatroban (RAM) influenced basal HA levels (ns, compared with untreated, open bar). Fibroblasts treated with either PGD$_2$ (5 µM) or PGJ$_2$ (2 µM) significantly increased HA synthesis (FIG. 5C, compared with FIGS. 1A-B and 4B). Pretreatment with the DP1 antagonist MK-0524 completely blocked the ability of both PGD$_2$ and PGJ$_2$ to induce HA production in orbital fibroblasts. By contrast, pretreatment with the DP2 antagonist Ramatroban was unable to prevent the induction of HA by PGD$_2$ or PGJ$_2$. This demonstrates that DP1 is the dominant receptor subtype involved in the induction of HA by D and J series prostaglindins.

Figure 5D:
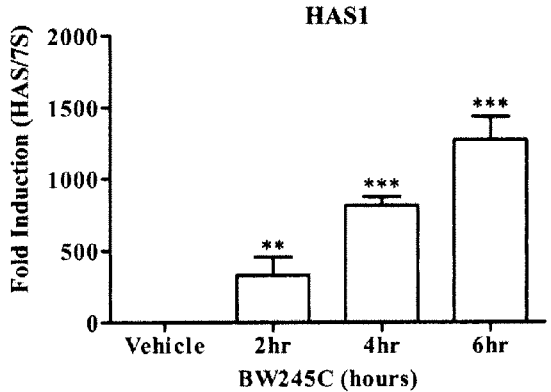
Figure 5E:
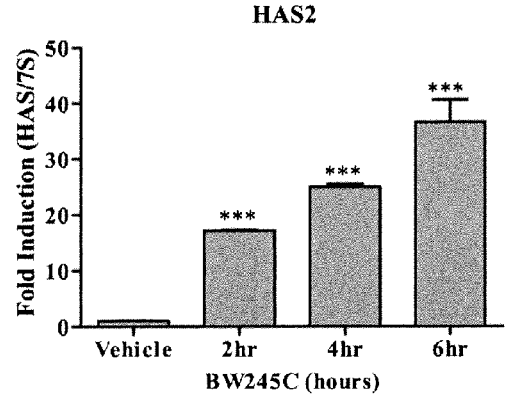
Figure 5F:
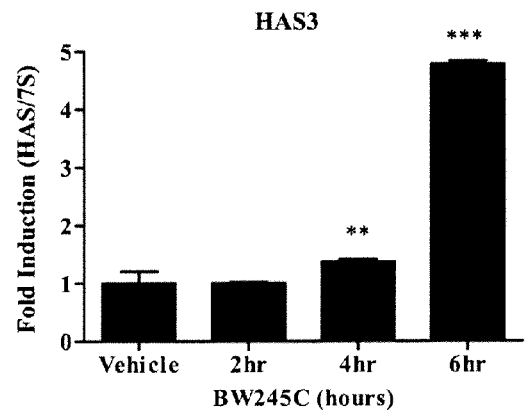
Figure 5G:
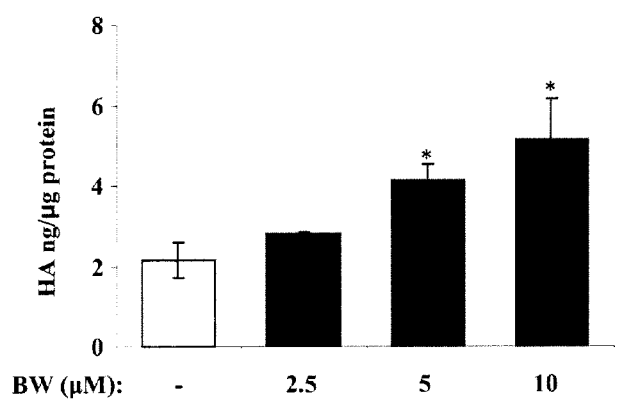

To confirm the importance of DP1 on the induction of HA in human orbital fibroblasts, the selective DP1 agonist BW245C (Kabashima et al., *Prostaglandins Leukot Essent Fatty Acids* 69(2-3):187-194 (2003), which is hereby incorporated by reference in its entirety) was used to treat OF and then HAS mRNA expression and HA production was assessed. The results presented in FIGS. 5D-F demonstrate that treatment with BW245C (10 µM) significantly induced HAS mRNA expression. Here, there was a significant increase in HAS1 and HAS2 mRNA expression as early as two hours (FIGS. 5D-E). HAS3 mRNA increased by 6 hours of exposure to BW245C (FIG. 5F). In addition, BW245C dose-dependently increased HA levels (FIG. 5G). At concentrations of 5 µM and 10 µM, there was a significant increase in HA production, compared to untreated fibroblasts.

In contrast, the high-affinity selective DP2 agonist DK-PGD$_2$ (Cheng et al., *Proc Natl Acad Sci USA* 103(17):6682-6687 (2006); Yoshimura-Uchiyama et al., *Clin Exp Allergy* 34(8):1283-1290 (2004); Hirai et al., *J Exp Med* 193(2):255-261 (2001), each of which is hereby incorporated by reference in its entirety), in the low µM concentration range, did not significantly increase HA levels. Taken together, these data provide strong evidence that PGD$_2$ and PGJ$_2$ induce HA production in orbital fibroblasts through activation of the DP1.

Figure 6A:
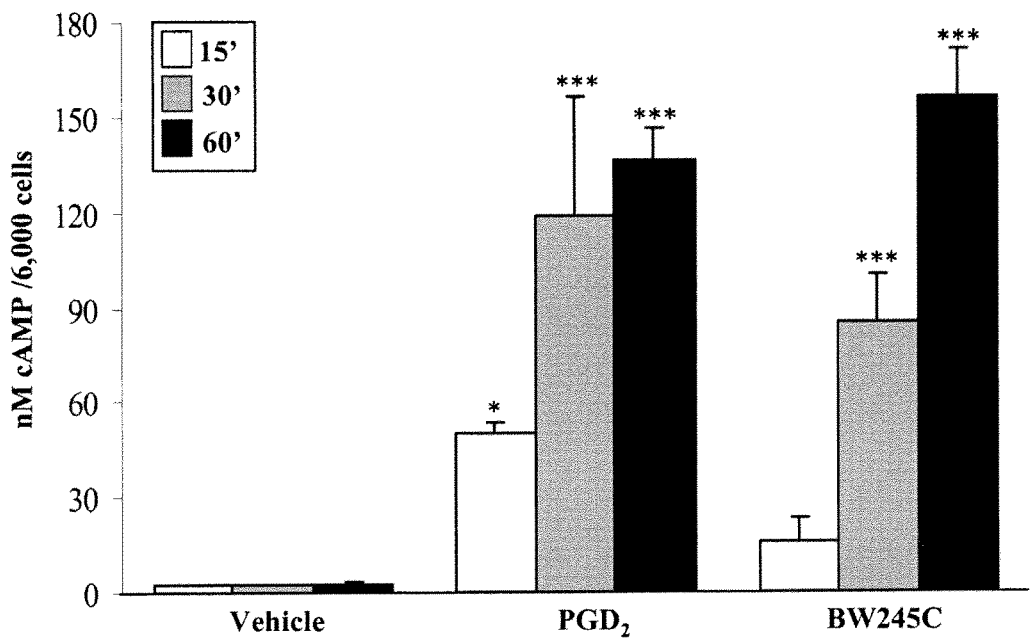
FIGS. 6A-B are graphs showing that $PGD_2$-induced HA synthesis is through the DP1-cAMP signal pathway.

Example 6—DP1 Activation Boosts Intracellular cAMP to Increase HA by Orbital Fibroblasts Activation of DP1, a Gs-protein coupled receptor, is known to lead to an increase in intracellular cAMP. It was therefore explored whether activation of DP1 by $PGD_2$, and subsequent production of HA, would require the generation of cAMP. Intracellular cAMP was measured following treatment with $PGD_2$ and the DP1 agonist BW245C. Treatment with $PGD_2$ (5 µM) and BW245C (10 µM) significantly increased intracellular cAMP production within 15 to 30 minutes (FIG. 6A). cAMP levels remained elevated through 60 minutes (FIG. 6A, black bars).

Figure 6B:
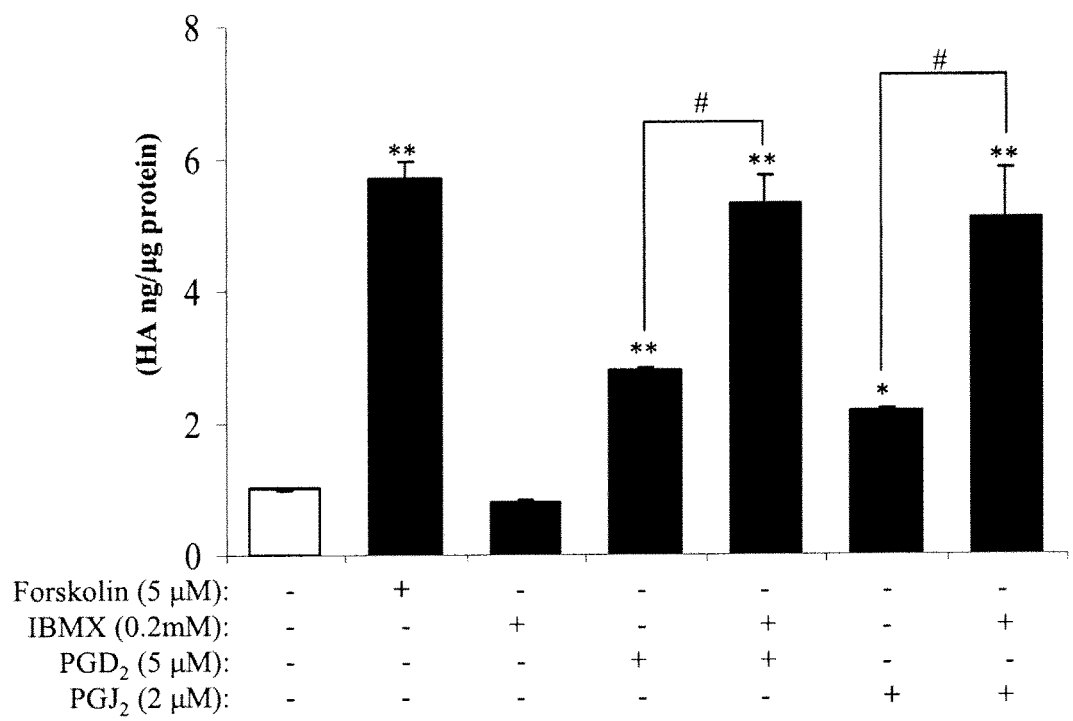

To investigate whether or not the elevation in intracellular levels of cAMP was directly attributable to the increased HA production by orbital fibroblasts, cells were treated with forskolin, which activates adenylyl cyclase to augment intracellular levels of cAMP (Morris et al., *Acta Physiol Scand* 181(4):369-373 (2004); Metzger et al., *Arzneimittelforschung* 31(8):1248-1250 (1981), which is Hereby Incorporated by reference in its entirety). Forskolin alone significantly increased HA production compared to vehicle-treated fibroblasts (FIG. 6B). Cells were treated with either $PGD_2$ or $PGJ_2$ together with IBMX, a nonselective phosphodiesterase inhibitor that boosts cAMP levels by preventing its degradation (Weinberg et al., *J Cell Biochem* 108(1):207-215 (2009), which is hereby incorporated by reference in its entirety). IBMX, in conjunction with either $PGD_2$ or $PGJ_2$, significantly enhanced the ability of $PGD_2$ or $PGJ_2$ to generate HA (FIG. 6B). Collectively, these data support the belief that $PGD_2$ and $PGJ_2$, via activation of DP1 and generation of cAMP, increase in HA production in human orbital fibroblasts.

Example 7—Mast Cell-Derived $PGD_2$ Activates Orbital Fibroblasts to Produce HA Via HAS2

Mast cells are a key immune cell proposed to be involved in the pathogenesis of TED via their ability to activate fibroblasts. Mast cells are also a key cell type that produces $PGD_2$ in vivo. Based on the results in the preceding examples, it was believed that mast cell-derived $PGD_2$ would increase HA production by orbital fibroblasts.

Figure 7A:
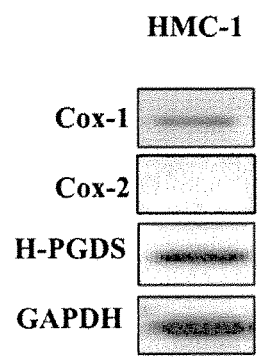
FIGS. 7A-B demonstrate that $PGD_2$ production by mast cells is dependent on H-PGDS activity.
Figure 7B:
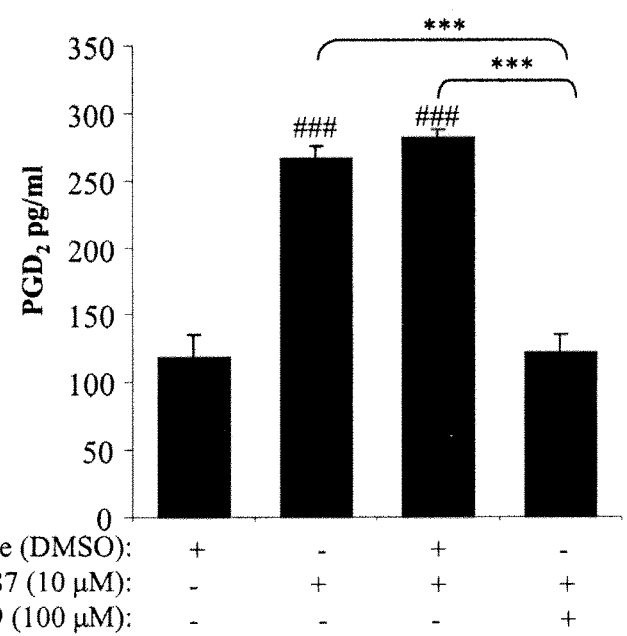

It was first determined whether human mast cells produce $PGD_2$ in vitro. HMC-1 cells, a commonly used human mast cell line (Kim et al., *Toxicol In Vitro* 23(7):1215-1219 (2009); Margulis et al., *J Immunol* 183(3):1739-1750 (2009), each of which is hereby incorporated by reference in its entirety), were used to first examine whether mast cells express H-PGDS. Western blot analysis of unstimulated HMC-1 cells revealed that these cells basally express both Cox-1 and H-PGDS, the hematopoietic-type PGDS (FIG. 7A). HMC-1 cells were then activated with A23187, a calcium ionophore (Kim et al., *Toxicol In Vitro* 23(7):1215-1219 (2009), which is hereby incorporated by reference in its entirety), in the presence or absence of HQL-79, a specific inhibitor of H-PGDS (Kanaoka et al., *Prostaglandins Leukot Essent Fatty Acids* 69(2-3):163-167 (2003); Aritake et al., *J Biol Chem* 281(22):15277-15286 (2006), each of which is hereby incorporated by reference in its entirety), and $PGD_2$ production determined. FIG. 7B demonstrates that activated HMC-1 cells significantly increase $PGD_2$ compared to unstimulated cells. Inhibition of H-PGDS with HQL-79 significantly reduced the level of $PGD_2$ in activated HMC-1 cells (FIG. 7B).

Figure 8A:
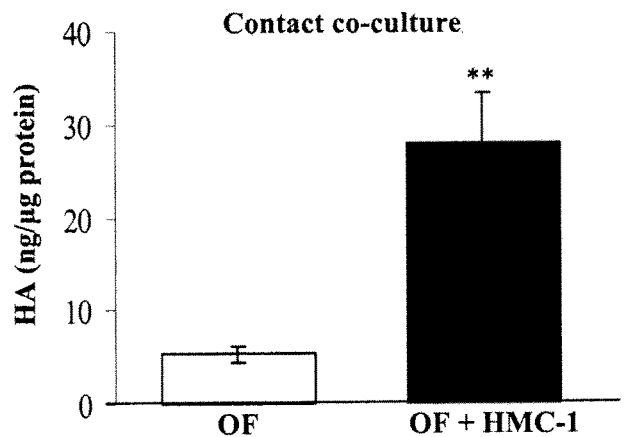
FIGS. 8A-C illustrate the ability of mast cell-derived $PGD_2$ to activate orbital fibroblast production of HA.

Using co-culture, the association between mast cells, orbital fibroblasts, and HA production was further investigated. First, orbital fibroblasts were cultured with HMC-1 cells (at a ratio of 1:1) for 4 hours. Following removal of the mast cells and addition of fresh media, the supernatant was collected for HA analysis. When fibroblasts and mast cells were cultured together, there was a significant increase HA production compared to fibroblasts alone (FIG. 8A, open versus black bar, **$p<0.001$).

A transwell system was then tested, whereby orbital fibroblasts were physically separated from HMC-1 cells. Following 24 hours of co-culture, conditioned media in both chambers was collected for HA ELISA. HA levels were negligible in the chamber (upper) containing only the HMC-1 cells. HA production also did not increase as a consequence of increasing cell number (FIG. 8B, open bars), indicating that HMC-1 cells do not produce HA in significant quantities. In contrast, HA levels in the lower chamber (orbital fibroblasts) were significantly higher than in the HMC-1 (upper) chamber (FIG. 8B; ###$p<0.001$ upper chamber compared to lower chamber). Co-culture of HMC-1 cells with orbital fibroblasts significantly increased HA levels with increasing ratios of HMC-1: orbital fibroblasts. Thus, even when HMC-1 cells were physically separated from fibroblasts, HA levels increased, suggesting that one or more factors secreted by the HMC-1 cells drives HA synthesis by fibroblasts.

Figure 8B:
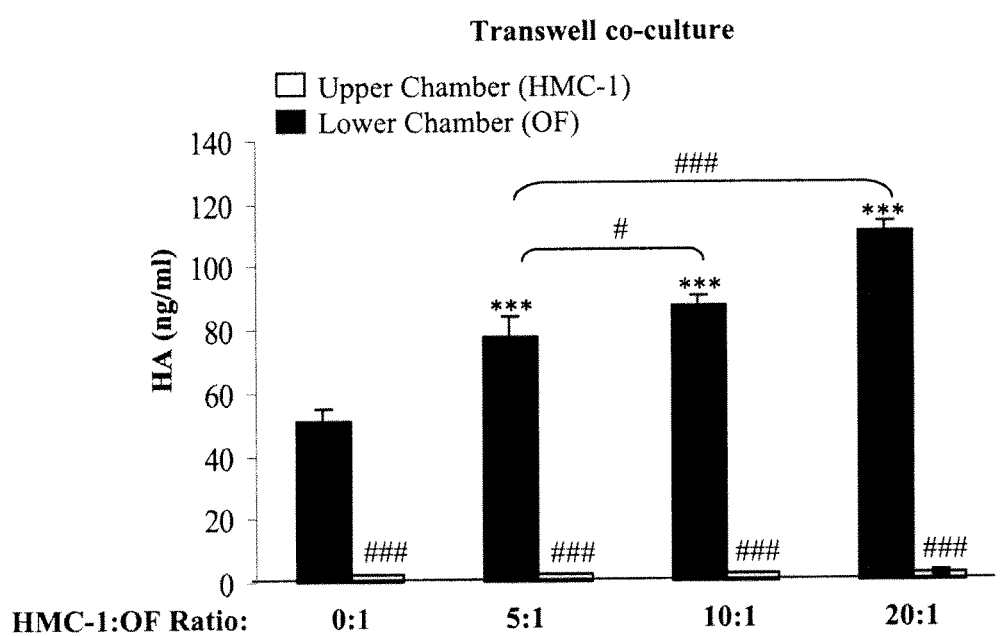
Figure 8C:
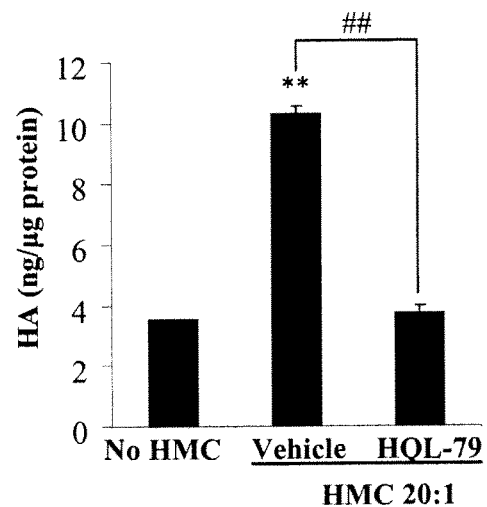

To determine if $PGD_2$ was the factor secreted by HMC-1 cells that was responsible for driving HA synthesis by orbital fibroblasts, HMC-1 cells were pretreated with HQL-79 (to block $PGD_2$ synthesis) and then these cells were added to the upper chamber of the transwell at a ratio 20:1 (HMC-1: orbital fibroblast). FIG. 8C shows that treatment of HMC-1 cells with HQL-79 significantly attenuated the production of HA by orbital fibroblasts compared to treatment of HMC-1 cells with vehicle alone. These data demonstrate that $PGD_2$ secreted by mast cells plays a dominant role in HA production by orbital fibroblasts during TED pathogenesis.

Figure 9:
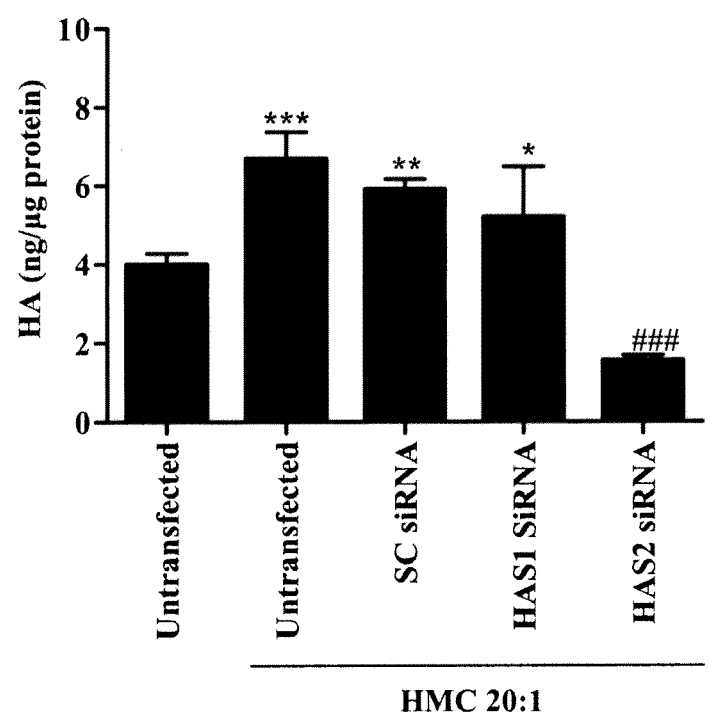
FIG. 9 is a graph showing that siRNA against orbital fibroblast HAS2 prevents mast cell-derived $PGD_2$ induction of HA. Orbital fibroblasts were transfected with HAS1, HAS2 or scrambled control (SC siRNA) siRNA using Lipofectamine 2000 (Invitrogen). Following this, the fibroblasts were co-cultured for 24 hours with HMC-1 cells in a transwell system at a ratio of 20:1 (mast cells: orbital fibroblasts) and the media collected for HA detection. Untransfected orbital fibroblast co-cultured with HMC-1 cells significantly increased HA production (*p<0.0001, compare untransfected to untransfected with HMC). Co-culture of fibroblasts with HMC-1 cells also induced a significant increase in HA in control siRNA-transfected (SC siRNA) (p<0.001) and HAS1 siRNA-transfected (*p<0.05) orbital fibroblasts. HAS2 siRNA-transfected orbital fibroblasts failed to increase HA synthesis when co-cultured with HMC-1 cells (###p<0.0001, compared to untransfected, control siRNA and HAS1 siRNA). Results are expressed as mean±SD (n=4-6).

Finally, to determine whether HA production by co-culture of fibroblasts with mast cells was via HAS2, orbital fibroblasts were transfected with control, HAS1 or HAS2 siRNA and the transfected fibroblasts were co-cultured with the mast cells. As expected, co-culture with untransfected fibroblasts with HMC-1 cell significantly increased HA production (FIG. 9). Transfection of fibroblasts with either control siRNA or HAS1 siRNA failed to attenuate HA production elicited by co-culture with HMC-1 mast cells. In contrast, transfection of orbital fibroblasts with HAS2 siRNA significantly decreased HA production by orbital fibroblasts. Here, there was a significant decrease in HA levels in basal (untransfected, no mast cells) as well as by fibroblasts co-cultured with HMC-1 cells (FIG. 9). Collectively, these data highlight the dominant role of HAS2 in HA production elicited by mast cell-derived $PGD_2$.

Discussion of Examples 1-7

TED is a debilitating disorder that causes disfigurement and vision impairment. TED afflicts approximately 40% of patients with Graves' hyperthyroidism, a thyroid-specific autoimmune disease characterized by the presence of auto-antibodies against the thyroid-stimulating hormone receptor. Treatment of moderate to severe TED often involves invasive procedures, including orbital radiotherapy and orbital decompression surgery (Bartalena et al., *N Engl J Med* 360(10):994-1001 (2009), which is hereby incorporated by reference in its entirety). There are few effective pharmacological treatments for TED due, in part, to a poor understanding the pathogenic mechanisms leading to clinical manifestations of TED. Current evidence suggests that activation of orbital fibroblasts by infiltrating inflammatory cells, particularly T cells and mast cells, plays an important role in TED pathogenesis (Hwang et al., *Invest Ophthalmol Vis Sci* 50(5):2262-2268 (2009); Feldon et al., *Invest Ophthalmol Vis Sci* 46(11):3913-3921 (2005); Lehmann et al., *Thyroid* 18(9):959-965 (2008), each of which is hereby incorporated by reference in its entirety). Orbital fibroblast proliferation and ECM production, particularly HA (Feldon et al., *Am J Pathol* 169(4):1183-1193 (2006); Gianoukakis et al., *Endocrinology* 148(1):54-62 (2007); Kaback et al., *J Clin Endocrinol Metab* 84(11):4079-4084 (1999), each of which is hereby incorporated by reference in its entirety), are key events that contribute to manifestations of TED, such as periorbital edema, exophthalmos and extraocular motility dysfunction (Prabhakar et al., *Endocr Rev* 24(6):802-835 (2003); van Steensel et al., *Invest Ophthalmol Vis Sci* 50(7):3091-3098 (2009), which is hereby incorporated by reference in its entirety). The data from Examples 1-7 above provide substantial evidence that mast cell-derived $PGD_2$ is a key factor that regulates the production of HA by orbital fibroblasts via activation of DP1 (FIGS. 1A-B, 5A-C, and 7B). Importantly, prevention of DP1 signaling (FIG. 5C) or $PGD_2$ production by mast cells (FIG. 8C) attenuated HA synthesis by the fibroblasts.

HA is a large negatively charged polysaccharide that is overproduced in the retroocular space of patients with TED (Kahaly et al., *Thyroid* 8(5):429-432 (1998), which is hereby incorporated by reference in its entirety). HA has remarkable viscosity and ability to retain water, which leads to increases in orbital tissue volume and anterior displacement of the eye, culminating in exophthalmos (Smith et al., *J Clin Endocrinol Metab* 89(10):5076-5080 (2004), which is hereby incorporated by reference in its entirety). Fibroblasts are the major source of HA in the orbit. Activation of orbital fibroblasts by immunoglobulins from TED patients (Smith et al., *J Clin Endocrinol Metab* 89(10):5076-5080 (2004), which is hereby incorporated by reference in its entirety) and cytokines such as interleukin-10 (Kaback et al., *J Clin Endocrinol Metab* 84(11):4079-4084 (1999), which is hereby incorporated by reference in its entirety), interferon-γ (Smith et al., *J Clin Endocrinol Metab* 72(5):1169-1171 (1991), which is hereby incorporated by reference in its entirety) and transforming growth factor-0 (Wang et al., *J Cell Biochem* 95(2):256-267 (2005), which is hereby incorporated by reference in its entirety) increase HA production. It is believed that the data presented in the preceding examples are the first to show that $PGD_2$, a non-cytokine mediator, contributes to HA synthesis by orbital fibroblasts (FIGS. 1A-C). The increase in HA production by $PGD_2$ is directly related to increased expression of HAS2 (FIGS. 3A, 3C, 4B, and 9). Despite the fact that all three HAS isoforms (HAS1, HAS2 and HAS3) are significantly increased, only the attenuation of HAS2 expression completely abrogated $PGD_2$-induced HA. This is in agreement with observations made in $HAS2^{-/-}$ mouse embryos, which are virtually devoid of HA (Camenisch et al., *J Clin Invest* 106(3):349-360 (2000), which is hereby incorporated by reference in its entirety). Of interest, HAS1 mRNA exhibited the most dramatic increase in response to $PGD_2$, yet does not contribute significantly to HA biosynthesis (FIG. 4B). This observation may be explained by the fact that HAS1 protein rapidly loses its enzymatic activity (Itano et al., *J Biol Chem* 274(35):25085-25092 (1999), which is hereby incorporated by reference in its entirety). Thus, these data provide compelling evidence that HAS2 is responsible for most, if not all, HA production by orbital fibroblasts in response to $PGD_2$.

The induction of HAS mRNA, and subsequent production of HA, required the generation of the second messenger cAMP via activation of DP1. DP receptors are expressed on orbital fibroblasts (FIGS. 5A-B); this property of orbital fibroblasts was not previously known. Pharmacological activation of DP1 significantly increased HAS mRNA and HA biosynthesis (FIG. 5C). Moreover, the DP1 antagonist MK-0524 completely inhibited $PGD_2$-induced HA production whereas DP2 antagonist Ramatroban had no effect. These findings provide substantial evidence that $PGD_2$-induced HA production is mediated solely by DP1. MK-0524 (also known as Laropiprant and CORDAPTIVE™) is an orally-acting drug that is currently being developed in conjunction with niacin as a cholesterol-lowering drug (Schwartz et al., *Am J Ther* 16(3):215-223 (2009), which is hereby incorporated by reference in its entirety). These results indicate that selectively targeting the DP1 system (via MK-0524 or any other similar acting pharmaceutical agents) in the eye should prevent the severity and/or occurrence of proptosis in TED patients by reducing HA production.

$PGD_2$ also regulates the migration of inflammatory cells by facilitating vasodilatation and increasing vascular permeability (Ulven et al., *Curr Top Med Chem* 6(13):1427-1444 (2006), which is hereby incorporated by reference in its entirety). Within the eye, this would facilitate transendothelial migration of infiltrating mast cells and lymphocytes, thereby contributing to the increase in immune cells characteristic of TED. Association of mast cells with fibroblasts/adipocytes in the orbital tissue is commonly observed in biopsies of TED patients as well as animal models of TED (Lauer et al., *Ophthal Plast Reconstr Surg* 24(4):257-261 (2008); Boschi et al., *Br J Ophthalmol* 89(6):724-729 (2005); Hufnagel et al., *Ophthalmology* 91(11):1411-1419 (1984); Many et al., *J Immunol* 162(8):4966-4974 (1999); Costagliola et al., *J Clin Invest* 105(6):803-811 (2000); Yamada et al., *Autoimmunity* 35(6):403-413 (2002), each of which is hereby incorporated by reference in its entirety). Mast cell degranulation and close proximity to adipocytes are suggestive of their participation in the TED process (Boschi et al., *Br J Ophthalmol* 89(6):724-729 (2005), which is hereby incorporated by reference in its entirety).

The data presented in the preceding examples strongly support the belief that mast cell:fibroblast interactions participate in TED. It was first demonstrated that fibroblasts robustly respond to $PGD_2$ to increase HA synthesis (FIG. 1A). Using both a co-culture and transwell system, it was also demonstrated that mast cells increase orbital fibroblast production of HA via $PGD_2$ produced by the mast cell (FIG. 8A-C). This accumulated HA within the orbit can, in turn, facilitate inflammatory cell infiltration (Toole, *Nat Rev Cancer* 4(7):528-539 (2004), which is hereby incorporated by reference in its entirety) to the orbit, thereby perpetuating clinical symptoms associated with TED. These data highlight $PGD_2$ as a key regulator of orbital fibroblast function.

It has been well-described that fibroblasts are heterogeneous, differing not only between organ systems but also within a given organ (Smith et al., *J Clin Endocrinol Metab* 80(9):2620-2625 (1995); Phipps et al., *J Periodontal Res* 32(1 Pt 2):159-165; Borrello et al., *Cell Immunol* 173(2): 198-206 (1997); Hagood et al., *Chest* 120(1 Suppl):64S-66S (2001); Khoo et al., *Thyroid* 18(12):1291-1296 (2008), each of which is hereby incorporated by reference in its entirety). In a previously publication it was shown that fibroblasts from the lung exhibit significant inter-individual variability in their apoptotic response to cigarette smoke (Baglole et al., *Am J Physiol Lung Cell Mol Physiol* 291(1):L19-29 (2006), which is hereby incorporated by reference in its entirety), a finding that may explain why only a fraction of smokers develop lung diseases such as chronic obstructive pulmonary disease (COPD). Therefore, it is noteworthy that there was significant variability in HA production, HA size and HYAL expression between orbital fibroblasts derived from two different individuals (FIGS. 1A-C and FIG. 2). The increase in low MW HA by OF1 (FIG. 1B) correlates with increased expression of HYAL1-3 (FIG. 2). These enzymes are responsible for the depolymerization of HA, thereby generating HA fragments (Noble, *Matrix Biol* 21(1):25-29 (2002), which is hereby incorporated by reference in its entirety). These low MW HA fragments are known to promote inflammation (de la Motte et al., *Am J Pathol* 174(6):2254-2264 (2009), which is hereby incorporated by reference in its entirety) by activating immune cells and increasing inflammatory gene expression (Gao et al., *J Biol Chem* 283(10):6058-6066 (2008), which is hereby incorporated by reference in its entirety). Thus, increased HA production, coupled with the generation of inflammation-promoting low MW HA, by orbital fibroblasts from an individual could be a decisive factor in predicting which Graves' patients ultimately develop symptomatic TED.

Using a combination of molecular and pharmacological approaches, the data presented herein illustrate a role for mast cell-derived $PGD_2$ in promoting HA biosynthesis by orbital fibroblasts, key effector cells in the pathogenesis of TED. The data also shows that the DP1/cAMP signaling pathway rapidly activates HAS mRNA induction to promote HA production. $PGD_2$, in addition to causing HA accumulation, may also provide an environment conducive of lymphocytes infiltration into orbital tissue via DP1. The lymphocytic accumulation within the orbit may, in turn, lead to additional release of inflammatory mediators, including $PGD_2$. Therefore, selectively targeting the production of lipid mediators (i.e., $PGD_2$) and/or activation of receptor systems (DP1) should reduce or prevent symptoms associated with TED.

Materials and Methods for Example 8-15

Materials

Rosiglitazone and GW9662 were purchased from Cayman Chemical (Ann Arbor, Mich.). Pioglitazone HCL was purchased from ChemPacific (Baltimore, Md.). Recombinant human TGF-β1 was purchased from Calbiochem (EMD bioscience, La Jolla, Calif.). [$^3$H] glucosamine hydrochloride was purchased from PerkinElmer Life Sciences. Hyaluronic acid potassium salt from human umbilical cord and *Streptomyces* hyaluronidase (HA'ase) were purchased from Sigma (St. Louis, Mo.). Unlike other hyaluronidases, this enzyme is specific for HA and is not active with chondroitin and chondroitin sulfate substrates (Ohya et al., *Biochim Biophys Acta.* 198(3):607-609 (1970), which is hereby incorporated by reference in its entirety).

Tissue Collection and Orbital Fibroblast Cell Culture

Orbital fibroblasts: Primary orbital fibroblasts were isolated from TED patients undergoing orbital decompression surgery. The protocol for orbital biopsy and blood sample isolation, described below, was approved by the Internal Review Board and informed, written consent was obtained from all patients. The primary fibroblasts were established by standard explant techniques (Smith et al., *J Clin Endocrinol Metab* 80(9): 2620-2625 (1995); Baglole et al., *Methods Mol Med* 117:115-27 (2005), each of which is hereby incorporated by reference in its entirety) and cultured in RPMI 1640 supplemented with 10% fetal bovine serum (FBS) (Hyclone, Logan Utah), 2-mercaptoethanol (Eastman Kodak, Rochester, N.Y.), L-glutamine (Life Technologies, Grand Island, N.Y.), HEPES (US Biochemical Corp., Cleveland, Ohio), nonessential amino acids, sodium pyruvate, and gentamicin (Life Technologies). Fibroblasts were characterized by their adherent morphology, expression of vimentin and collagen (types I and III) and absence of CD45, factor VIII and cytokeratin. Fibroblasts were used at the earliest passage possible (between passages 4 to 10). Human peripheral blood T cells: One unit of blood was obtained from healthy donors as approved by the University of Rochester Institutional Review Board and Office for Human Subjects Protection. Peripheral blood mononuclear cells (PBMC) were obtained by density-gradient centrifugation of buffy coat using Ficoll-Paque Plus (Amersham Biosciences, Piscataway, N.J.). PBMCs were washed in PBS and T cells were enriched using CD3/CD28 T cell Expander beads (Dynal Inc., Brown Deer, Wis.). Specifically, $5 \times 10^6$ PBMCs were incubated with CD3/CD28 beads at ratio 1:1 in RPMI1640 with 10% FBS medium at 37° C. for 2 days. After that, 50 U rIL-2/ml was added to the culture and incubated for another 2 or 3 days. On day 5, cells were diluted to $0.5 \times 10^6$/ml in culture medium containing 50 U/ml rIL-2 and incubated for another 3-7 days according to the cell number. After T-cell expansion, the cells were examined for purity by staining with an anti-CD3 phycoerythrin-labeled antibody (BD Biosciences, San Jose, Calif.). The T cell purity was >95%.

Cell Viability Assay

Cell viability was assayed using the colorimetric XTT (2,3-bis-(2-methoxy-4-nitro-5-sulfophenyl)-2H-tetrazolium-5-carboxanilide) assay kit (Roche, Germany). Briefly, orbital fibroblasts were seeded in a 96-well plate and cultured with various treatments. Twenty hours after treatment, 50 μl of XTT labeling mixture was added and cells were incubated at 37° C. for 4 hours. The amount of cleaved XTT product generated by metabolically active cells was assayed by measuring absorbance using an ELISA plate reader at 480 nm with a reference wavelength at 650 nm. Cell viability results were also confirmed by Trypan blue staining.

Flow Cytometry

Enriched human peripheral blood T lymphocytes were surface stained for CD3 (BD Biosciences, San Jose, Calif.) or CD44 (clone IM7, Biolegend, San Diego, Calif.) for 20 min at 4° C., washed in staining buffer (PBS with 0.3% BSA) and pelleted by centrifugation. Samples were run on a FACScalibur (BD Bioscience, San Jose, Calif.) flow cytometer and analyzed using FlowJo software (Tree Star).

Quantitation of HA

Confluent monolayers of orbital fibroblasts were serum starved in 0.5% FBS RPMI-1640 medium for three days and pretreated with different concentrations of Pio or Rosi for 1 hour and then treated with or without 2 ng/ml TGF-β1 for 24 hours. After treatments, an aliquot of culture medium (secreted HA) was removed and centrifuged at 8,000×g at 4° C. for 5 minutes and the supernatant was saved for later analysis. The cells were washed twice with PBS and treated with 0.25% trypsin-EDTA solution (GIBCO, Invitrogen) at 37° C. for 5 minutes, the reaction was stopped by addition of culture medium and cell number was determined using a hemocytometer. The cells were then centrifuged and the supernatant was collected and incubated at 100° C. for 10 minutes to inactivate trypsin activity. This supernatant was saved for pericellular HA detection. The cell pellet was washed with PBS once and digested with 120 μg/ml proteinase K in 0.1% SDS/0.1 M Tris-HCl (pH 7.6) at 37° C. for 1 hour, and proteinase K was inactivated by incubation at 100° C. for 10 min. The cell lysate was centrifuged and supernatant analyzed for intracellular HA.

The amount of HA in each extract (secreted HA, pericellular HA and intracellular HA) was measured by ELISA based on the specific interaction of HA with HA binding protein (HABP). The HA detection kit was purchased from R&D system (Minneapolis, Minn.). Briefly, diluted samples were incubated in HABP-coated microwells, allowing HA present in samples to react with the immobilized HABP. After extensive washing, biotinylated HABP was added to the microwells to form complexes with bound HA. Following another round of washing, streptavidin conjugated horseradish peroxidase was added. After a brief incubation period and washing, chromogenic substrate was added and HA levels were determined using a Varioskan Flash plate reader (Thermo Fisher Scientific, Milford, Mass.). A fraction of the samples were pretreated with *Streptomyces* hyaluronidase (2 U/ml at 37° C. for 2 hour) before subjected to the ELISA assay as a negative control. Furthermore, an additional 50 ng/ml (final concentration) of free soluble HA was added to a fraction of the cell lysate samples to confirm that there are no inhibitory factors present and that the assays show the expected additivity when a known amount of exogenous HA is included.

HA [$^3$H] Radiolabeling

Confluent monolayers of orbital fibroblasts were serum starved for three days and treated with or without 2 ng/ml TGF-β1 for 24 hours. One hour after TGF-β1 treatment, [$^3$H] glucosamine hydrochloride (PerkinElmer Life Sciences) was added to the medium to a final concentration of 20 µCi/ml. After labeling, the medium, trypsin extract solution and cell lysate were collected as described above. Radiolabeled macromolecules in each extract were concentrated using a Vivaspin 10 kDa cut-off ultrafiltration spin column (Sartorius Stedim Biotech, Goettingen, Germany) and washed with PBS twice. An equivalent radiolabeled aliquot was digested with *Streptomyces* hyaluronidase (2 U/ml) at 37° C. overnight before concentration. The concentrated solution was transferred to scintillation vials, and [$^3$H] incorporation was determined with a microplate scintillation counter (TopCount; PerkinElmer, Meriden, Conn.). Incorporation of [$^3$H]-glucosamine into HA was calculated by subtracting the counts from the *Streptomyces* hyaluronidase digested fraction.

T Cell Adhesion Assay

Preparation of peripheral blood mononuclear T cells. Enriched T cells (1×10$^7$ cells/ml) were fluorescently labeled by incubation with calcein-AM (10 µg/ml, Molecular Probes) for 45 min in RPMI 1640 medium without phenol red, and washed twice in RPMI 1640 medium with 0.5% FBS. After labeling, some T cells were incubated with monoclonal CD44 antibody (clone IM7, Biolegend, San Diego, Calif.) or isotype (Rat IgG2b) at dilution of 1:25 (final concentration is 40 µg/ml) at 37° C. for 15 minutes. Preparation of orbital fibroblasts. Confluent orbital fibroblasts in a 96-well plate were serum starved and incubated with different concentrations of Pio or Rosi treated with or without 2 ng/ml TGF 1 for 24 hours. In some cultures, orbital fibroblasts were treated with *Streptomyces* hyaluronidase (100 mU/ml at 37° C. for 1 hour) prior to the adhesion assay to deplete endogenous HA. Adhesion Test. Immediately before the adhesion assay, the conditioned medium of orbital fibroblasts was removed to eliminate treatments and secreted ECM. 1×10$^5$/well of Calcein AM labeled T cells were added to a 96-well plate with a confluent orbital fibroblast monolayer and allowed to adhere for 90 min at 4° C. as previously described. Plates were washed three times with the addition of 200 ul of PBS followed by plate inversion and gentle tapping to remove the wash solution. Fluorescence was measured with an excitation of 485 nm and detection of 535 nm, in a Varioskan Flash plate reader (Thermo Electron Corporation). There is a positive correlation between the labeled T cell number and fluorescence intensity ($r^2$ is >0.998), thus the number of T cells bound per well was calculated from the fluorescence intensity of the well.

Immunohistology

Orbital fibroblasts were cultured in 8-chamber slides (BD REF354108) and fixed in room temperature 3% paraformaldehyde in PBS and stained with 1 µg/ml biotinylated HABP (Seikagaku, Cape Cod) followed by Cy3-conjugated streptavidin (Jackson laboratories, West Grove, Pa.). F-actin was stained with Phalloidin (Molecular Probes). In some cultures, orbital fibroblasts were treated with *Streptomyces* hyaluronidase prior to staining. T cells were stained with an anti-CD3 monoclonal antibody (clone UCHT, SouthernBiotech, Birmingham, Ala.) followed by a goat anti-mouse antibody labeled with Alexa-488 (Molecular Probes). DAPI (10 µg/ml, Anaspec, San Jose, Calif.) was used for nuclear staining.

Orbital adipose tissues were obtained from TED patients undergoing orbital decompression surgery. The tissues were fixed in 3% paraformaldehyde in PBS at 4° C. for 1 hour and washed with PBS. Tissues were then saturated in 20% sucrose/PBS at 37° C. for 2 hours, embedded in OCT compound (Sakura Tissue Tek) and frozen in dry ice. Ten µm thick sections of frozen tissue were first incubated with biotinylated HABP, anti-CD44 and anti-CD3 monoclonal antibodies and the stained with Cy3-conjugated streptavidin, Alexa-488 conjugated donkey anti-rat antibody and Alexa-647 conjugated goat anti-mouse antibody. Some sections were pretreated with 2 U/ml *Streptomyces* hyaluronidase before staining or were added free soluble HA 200 m/ml to HABP probe to compete endogenous HA as HA negative control. Fat was stained with Bodipy 493/503 dye (Molecular Probes). Slides were photographed using a Carl Zeiss Axio Imager M1 Microscope.

Reverse Transcriptase PCR (RT-PCR) and Quantitative RT-PCR (qRT-PCR)

RNA was isolated from orbital fibroblast strains using the RNeasy Mini kit according to the manufacturer's protocol (Qiagen, Valencia, Calif.) and reverse transcribed to cDNA using iScript cDNA synthesis kit (Bio-Rad, Hercules, Calif.). Primers for human HAS1, 2, 3 and 7S as well as qRT-PCR method to detect relative abundance of mRNA are identified supra. Primers for human PPARγ1 (NM138711) and PPARγ 2 (NM015869) mRNA were 5'-AAAGAAGC-CGA-CACTAAACC-3' (SEQ ID NO:3) (sense), 5'-CTTC-CATTACGG-AGAGATCC-3' (SEQ ID NO:4) (antisense) and, 5'-GCGATTC-CTTCACTGATAC-3' (SEQ ID NO:5) (sense), 5'-CTTCCATT-ACGGAGAGATCC-3' (SEQ ID NO:6) (antisense), respectively.

mRNA Knockdown Using Small Interfering RNA (siRNA)

Orbital fibroblasts were cultured to 80-90% confluence and transfected with PPARγ SMARTpool siRNA and scramble control (SC) siRNA (Dharmacon). Final concentration of siRNA was 80 nM using Lipofectamine 2000 (Invitrogen) according to the instructions of the manufacturer. Forty-eight hours after transfection, the cells were serum starved for 48 hours and the medium was replaced with fresh medium containing 2 ng/ml TGF-β1, either with or without 10 µM Pio or 10 µM Rosi. After 24 hours incubation, the medium was collected and HA levels were analyzed by ELISA. For PPARγ mRNA detection, four days after transfection, RNA was prepared as above and PPARγ1 and PPARγ 2 mRNA levels were analyzed using Real-Time PCR. HAS1 and HAS2 siRNAs (Santa Cruz) were also used to knockdown HAS1 and HAS2 mRNA expression, respectively, as described supra. After 24 hours transfection, the cells were serum starved and treated with TGF-β1 for 24 hours before further experiment.

Statistical Analysis

Statistical analysis was performed using GraphPad Prism (GraphPad Software, Inc, La Jolla, Calif.). For comparison between groups of three or more, an analysis of variance (ANOVA) with a Newman-Keuls multiple comparison test was used to determine differences between treatments. Error bars represent the standard deviation from the mean of triplicate samples. A p value<0.05 is considered significant. All experiments were performed at least three times.

Figure 10A:
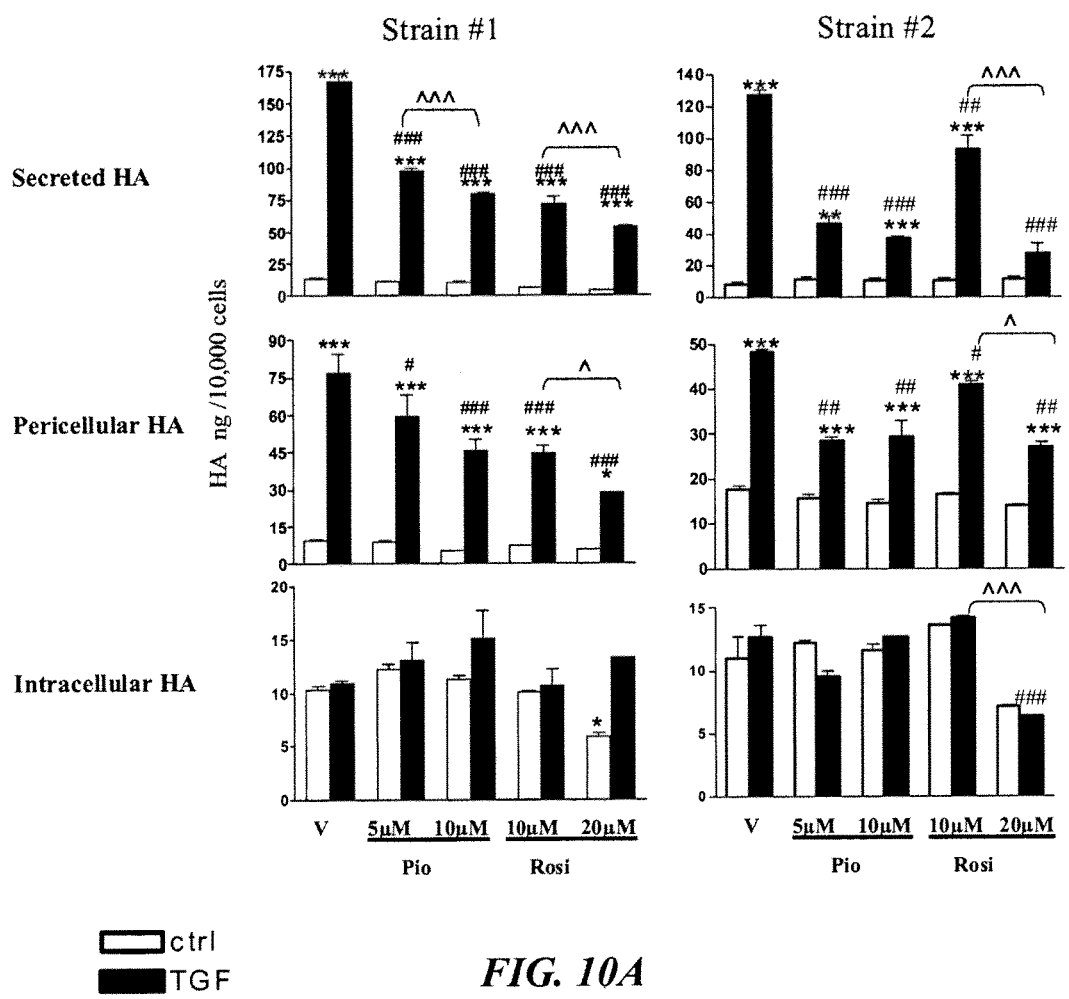
FIGS. 10A-B show that the PPARγ ligands Pio and Rosi inhibit TGF-β1 induced HA production in human orbital fibroblasts. Confluent strains of human orbital fibroblasts were cultured in RPMI-1640 with 0.5% FBS for 3 days prior to treatment with different concentrations of Pio or Rosi with or without 2 ng/ml TGF-β1 for 24 hours (FIG. 10A). The culture medium (secreted HA), cell trypsin solution (pericellular HA) and cell lysate (cellular HA) were assayed by an HA ELISA as described in the Experimental Procedures. TGF-β1 treated samples show a robust induction of secreted and pericellular HA levels. There was no significant change in intracellular HA levels. The experiment was performed in triplicate. *p<0.05, ***p<0.001 compared to vehicle control (V); #p<0.05, ###p<0.001, compared to TGF-β1 treatment; ^p<0.05, ^^^p<0.001, 5 µM Pio versus 10 µM Pio or 10 µM Rosi versus 20 µM Rosi; ns, no significant changes. Samples were run in duplicate utilizing three separate human orbital fibroblast strains (representative results are shown). Results are expressed as the mean±SD.

Example 8—TGF-β1 Induces HA Synthesis and Pio and Rosi Inhibit TGF-β1 Induced HA Biosynthesis in Human Orbital Fibroblasts To determine whether the PPARγ ligands Pio and Rosi might block TGF-β1 induced HA synthesis, several representative primary human orbital fibroblast strains were selected and then treated with 2 ng/ml TGF-β1 in the presence or absence of the PPARγ ligands Pio or Rosi at varying concentrations. Representative results from two fibroblast strain are show in FIG. 10A. HA, which is synthesized on the plasma membrane, can be secreted into the ECM, stay on the cell membrane or remain in the cell. HA levels were detected in the cell culture supernatant (secreted HA), in cell trypsin solution (pericellular HA), and in cell lysate (intracellular HA) using a commercial HA ELISA kit. FIG. 10A demonstrates that TGF-β1 significantly increased secreted and pericellular HA levels (p<0.001, upper and middle panel), respectively, but had no effect on intracellular HA levels (lower panel). In strain#1, TGF-β1 increased secreted HA levels 12.16±0.15 fold and increased pericellular HA levels 8.34±1.33 fold compared to vehicle control. There was 2.31±0.36 fold more secreted HA compared with pericellular HA in fibroblasts treated with TGF-β1. Strain#2 showed similar results (FIG. 10A). Therefore about 70% of the TGF-β1 mediated, newly synthesized HA was secreted into the ECM. The remaining newly synthesized HA was localized pericellularly on the cell surface. FIG. 10A also demonstrates that Pio or Rosi treatment alone has no significant effect on HA synthesis. However, treatment with Pio and Rosi substantially diminished the induction of secreted HA and pericellular HA by TGF-β1 in a dose-response manner. 10 µM Pio inhibited TGF-β1 mediated secretion and pericellular accumulation of HA by a 52±2.2% and 40±2.2%, respectively. Experiments using 10 µM Rosi instead of 10 µM Pio showed similar results (FIG. 10A). However, 20 µM Rosi significantly reduced intracellular HA levels in both strains.

To confirm the HA ELISA results, $^3$H-glucosamine, which is incorporated into newly synthesized HA, was used to compare HA levels between cell-associated and secreted HA levels. The results showed similar increases in HA accumulation.

Figure 10B:
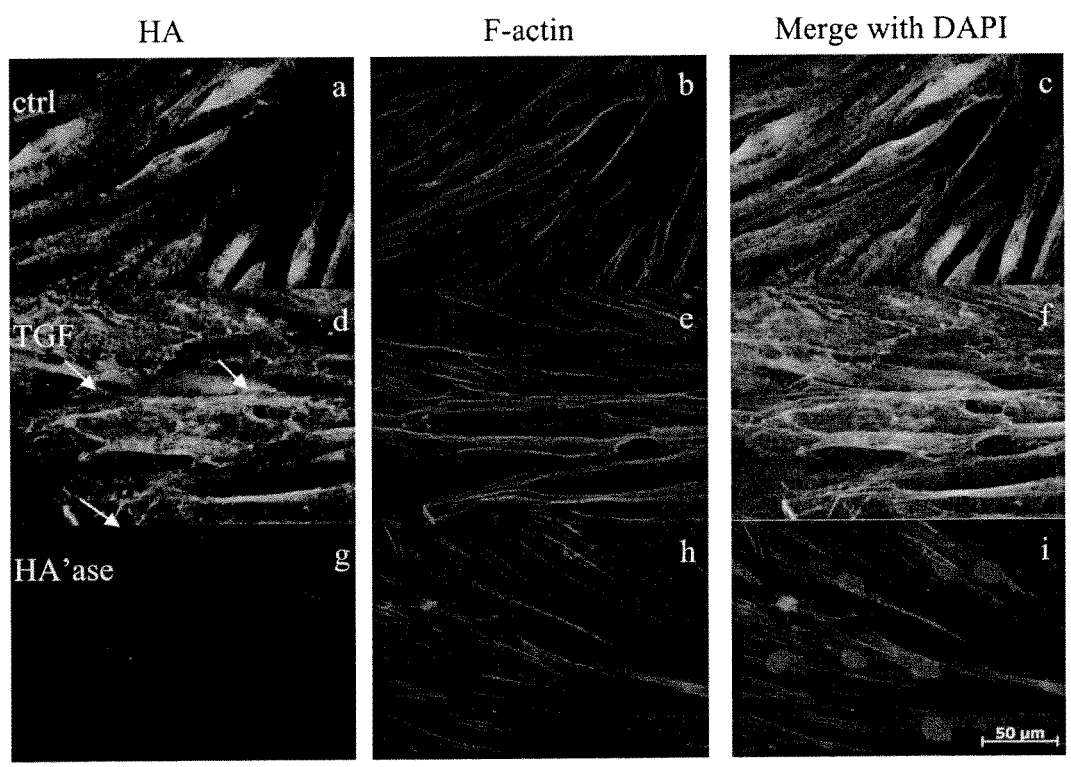

Immunofluorescence was also used to analyze HA expression. FIG. 10B shows untreated cells (top row) with HA staining (green) mainly around the nucleus. In TGF-β1 treated cells (middle row), HA staining is more pronounced and forms microvillus-like protrusions (Kultti et al., *J Biol Chem* 281(23):15821-15828 (2006), which is hereby incorporated by reference in its entirety). Cells treated with *Streptomyces* hyaluronidase before immunostaining (bottom row) did not show HA staining and furthermore did not affect stress fiber F-actin staining (red) or nuclear staining (blue), confirming specificity of the experiment. TGF-β1 treatment did not significantly alter F-actin levels or affect cell structure in this system as cells were only treated with TGF-β1 for 24 hours.

Example 9—Pio and Rosi Inhibit TGF-β1 Induced HAS1 and HAS2 mRNA Expression

The preceding examples demonstrate that increased HA production by $PGD_2$ is directly related to increased expression of HAS2 (FIGS. 3A, 3C, 4B, and 9).

Figure 11:
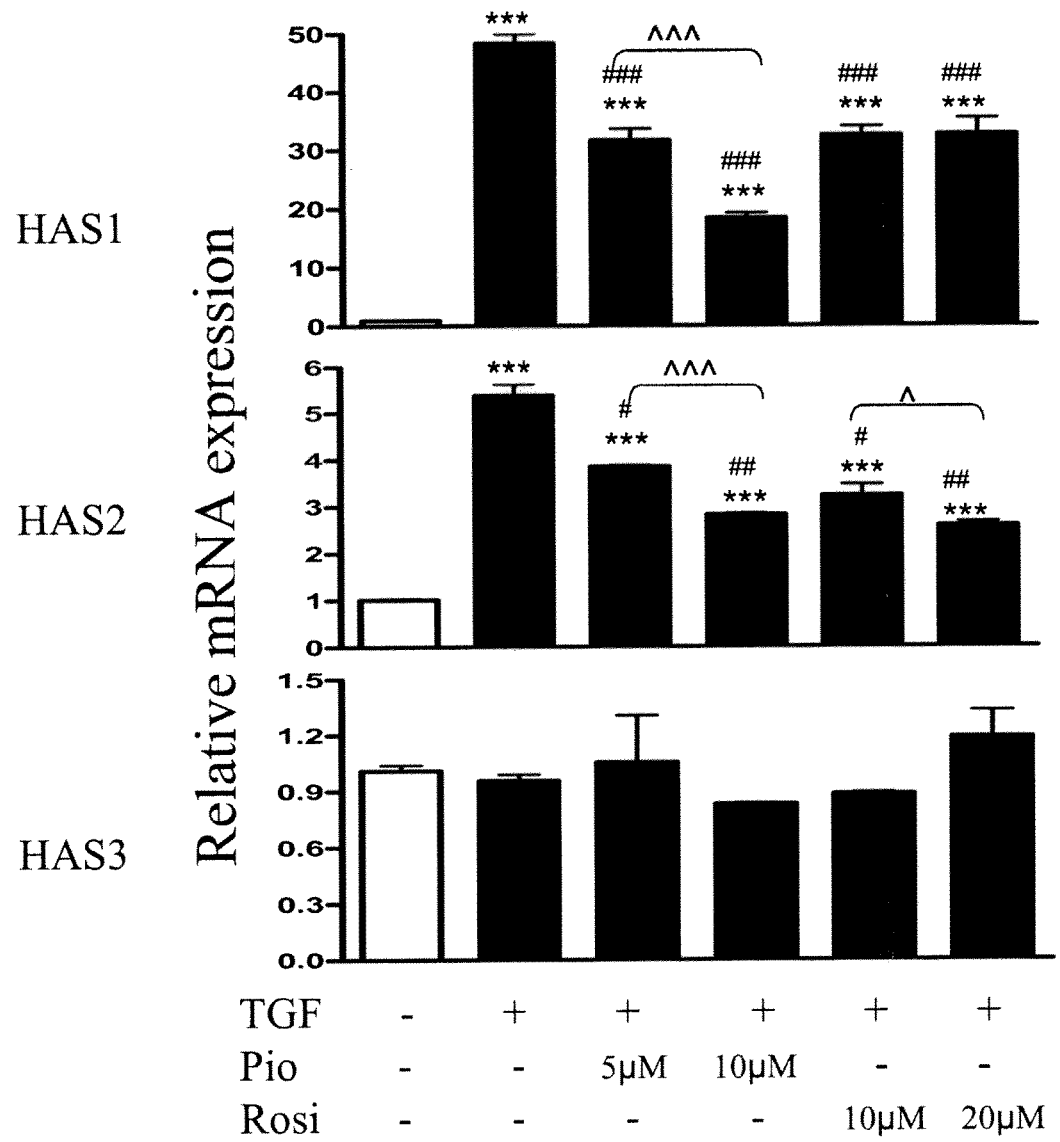
FIG. 11 is a panel of graphs showing that Pio and Rosi inhibit TGF-β1 induced HAS1 and HAS2 mRNA expression in human orbital fibroblasts. Total RNA from orbital fibroblasts treated with different concentrations of Pio or Rosi, with or without TGF-β for 6 hours was analyzed by qRT-PCR as described in the Experimental Procedures. White bar, no TGF-β1; black bars, 2 ng/ml TGF-β1. There was a significant increase in HAS1 and HAS2 mRNA levels (***p<0.001 compared to vehicle control) after TGF-β1 treatment. HAS3 has no significant change. This increase in HAS1 or HAS2 induced by TGF-β1 was significantly inhibited by Pio or Rosi (###p<0.001). Results are expressed as the mean±SD of triplicate samples performed on triplicate cultures.

To determine if the PPARγ ligands Pio and Rosi could inhibit TGF-β1 induced increases in HAS mRNA levels, fibroblasts were treated with 2 ng/ml TGF-β1 with or without Pio or Rosi for 6 hours and RNA was isolated and HAS expression was determined by Real-Time PCR. FIG. 11 shows that TGF-β1 strongly induced HAS1 and HAS2 mRNA levels, which increased about 50- and 6-fold, respectively, while HAS3 mRNA levels remained unchanged. Pio treatment significantly inhibited TGF-β1-induced HAS1 mRNA expression in a dose dependent manner, whereas Rosi treatment inhibited HAS1 mRNA expression similarly at both doses used (FIG. 11, top graph). Both Pio and Rosi treatment significantly inhibited TGF-β-induced HAS2 mRNA expression in a dose-dependent manner (FIG. 11, middle graph). 10 µM Pio inhibited TGF-β1 mediated HAS1 and HAS2 mRNA induction by approximately 50%. 10 µM Rosi had similar effects on HAS1 and HAS2 mRNA levels (FIG. 11).

Example 10—Pio and Rosi do not Influence Orbital Fibroblast Viability

Figure 12:
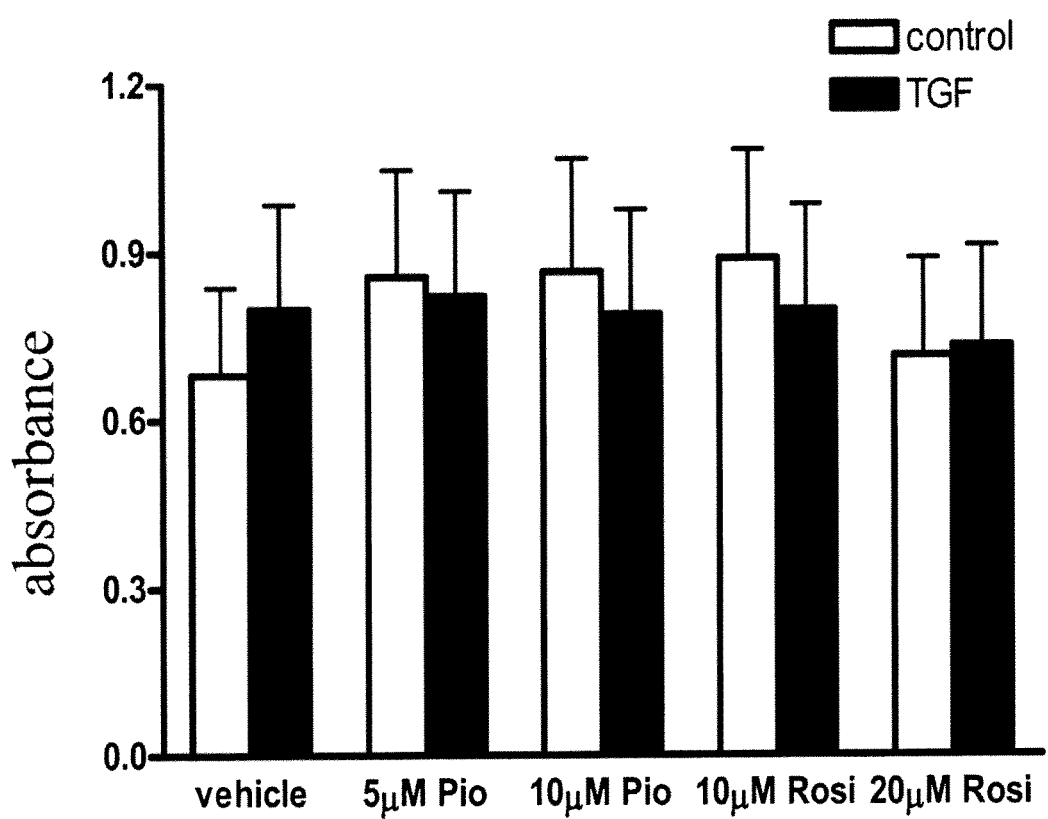
FIG. 12 is a graph showing that Pio and Rosi do not influence human orbital fibroblast viability. Confluent strains of human orbital fibroblasts were cultured in RPMI-1640 with 0.5% FBS for 3 days prior to treatment with different concentrations of Pio or Rosi with or without 2 ng/ml TGF-β1 for 24 hours. Viability was measured by XTT assay. Results shown are representative of 3 independent experiments and are mean±SEM (n=8). No significant differences were observed with any treatment (ANOVA). V: vehicle control.

To rule out the possibility that the reduction in HA synthesis is a result of toxicity by Pio and Rosi, viability of human orbital fibroblasts treated with the PPARγ ligands was measured by the XTT assay. Viable cells actively cleave the XTT reagent and form a water soluble orange formazan dye, the appearance of which is proportionate to the number of viable cells. As FIG. 12 demonstrates, after 24 hours treatment, there was no significant difference in cell viability among treatment conditions, with or without addition of TGF-β1. Furthermore, in the experiment for FIG. 10, cells were counted after each treatment to normalize HA production per cell. No significant changes in cell number were detected from cells treated with Pio or Rosi. Thus, there was no evidence of cell toxicity in orbital fibroblasts exposed to Pio and Rosi at the concentrations used.

Example 11—Pio and Rosi Inhibit TGF-β1 Induced HA Production Via a PPARγ-Independent Pathway One potential mechanism by which Pio and Rosi treatment decrease TGF-β1 induced HA production is through activation of PPARγ, since they are PPARγ ligands and PPARγ acts as a negative regulator of TGF-β (Sime, *J Investig Med* 56(2):534-538 (2008), which is hereby incorporated by reference in its entirety). GW9662 is a highly specific PPARγ antagonist that covalently binds to a cysteine residue within the ligand binding domain of PPARγ, permanently altering its ability to bind its ligands (Ferguson et al., *Am J Respir Cell Mol Biol* 41:722-731 (2009), which is hereby incorporated by reference in its entirety). It was previously reported that PPARγ ligand-driven adipogenesis is PPARγ dependent and is completely inhibited by GW9662 (Feldon et al., *Am J Pathol* 169(4):1183-11893 (2006), which is hereby incorporated by reference in its entirety). However, the addition of GW9662 did not significantly reduce the ability of either Pio or Rosi to inhibit TGF-β1 induced HA synthesis (FIG. 13A), providing compelling evidence that Pio and Rosi function through molecular pathways that are independent of PPARγ activation.

To confirm this result using a genetic approach, PPARγ specific siRNAs were introduced into orbital fibroblasts to downregulate PPARγ expression. Real-Time PCR demonstrated that PPARγ 1 and PPARγ 2 mRNA levels were decreased by more than 90% in PPARγ siRNA treated samples compared to control siRNA treated samples (FIG. 13B). PPARγ siRNA also inhibited orbital fibroblast adipogenesis driven by PPARγ ligands as demonstrated by oil red 0 staining. However, PPARγ siRNA did not influence HA production in orbital fibroblasts treated with or without TGF-β1 compared to control siRNA, and did not prevent the inhibition of TGF-β1 mediated HA production by Pio and Rosi (FIG. 13C). These data provide further evidence that Pio and Rosi mediated effects on HA production are PPARγ-independent.

Example 12—TGF-β1 Treated Orbital Fibroblasts Bind Activated Human T Cells Through HA-CD44 Interaction One of the hallmarks of TED is the infiltration of leukocytes (particularly T cells) into orbital tissue. Extracellular HA binds the cell surface receptor CD44 and promotes lymphocyte rolling and adhesion to sites of inflammation. Therefore, increased production of HA mediated by TGF-β1 prompted investigation of the possibility that TGF-β1 promotes T cell adhesion to orbital fibroblasts. Human peripheral blood T cells were activated using IL-2 and enriched by CD3/CD28 beads. The expression of CD44 and CD3 (T cell marker) were detected by flow-cytometry. FIG. 14A demonstrates that about 99% of the enriched human T cells are CD44 and CD3 positive, indicating that T cells have the potential to bind HA produced by orbital fibroblasts.

Next, the T cell adhesion assay was performed with human orbital fibroblasts. Orbital fibroblasts were treated with or without TGF-β1 for 24 hours. To eliminate the influence of TGF-β1 or other factors in conditioned medium, fresh medium was added to fibroblast cultures immediately before addition of T cells. To determine if HA is associated with the adhesion of T cells, a fraction of TGF-β1 treated fibroblast cultures were incubated with *Streptomyces* hyaluronidase to digest extracellular HA and a fraction of T cells were incubated with a monoclonal CD44 antibody or an isotype control to block the HA-CD44 binding site. T cells were pre-labeled with calcein-AM and added to fibroblast cultures and allowed to incubate at 4° C. for 90 minutes. FIG. 14B shows that adhesion of T cells to orbital fibroblasts treated with TGF-β1 significantly increased compared to untreated control fibroblasts. T cells preincubated with CD44 antibody adhered less to fibroblasts than did T cells preincubated with isotype control antibody (FIG. 14B, third bar, p<0.01). As another control, T cells were incubated with exogenous HA at 37° C. for 1 hour before being added to orbital fibroblasts. As expected, addition of 100 or 500 µg/ml exogenous HA significantly reduced T cell adhesion to orbital fibroblasts. Furthermore, pretreatment of fibroblast cultures with *Streptomyces* hyaluronidase, which completely digests extracellular HA, abolished TGF-β1-induced T cell adhesion (FIG. 14B, fifth bar, p<0.01). These data indicate that newly synthesized pericellular HA is required for cell-cell adhesion and that the HA-CD44 interaction plays an important role in T cell adhesion to orbital tissue. A non-fibroblast control was used to confirm that the binding is through cell-cell adhesion, not a cell-substratum adhesion.

Figure 15A:
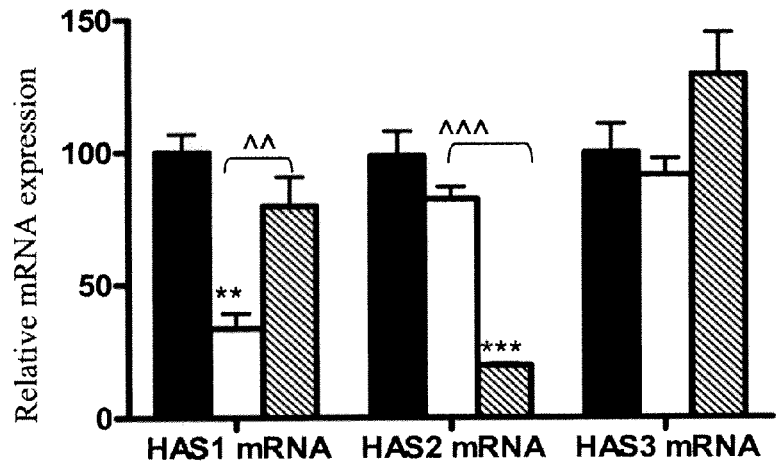
FIGS. 15A-C are graphs illustrating that TGF-β-induced HA production by orbital fibroblasts and T cell-fibroblast adhesion are dependent upon HAS2 expression.
Figure 15B:
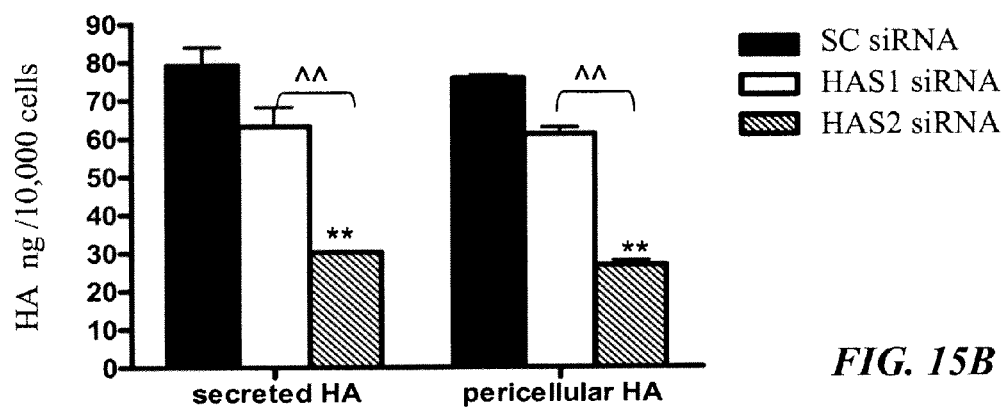
Figure 15C:
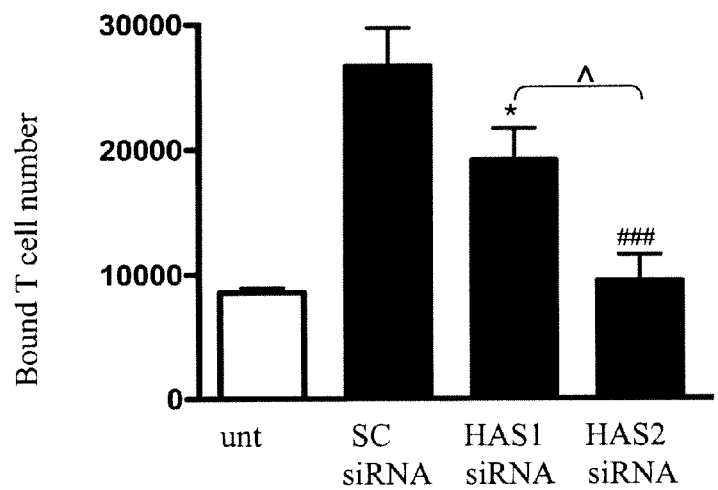

Example 13—TGF-β1 Induced Adhesion of Orbital Fibroblasts and Activated Human T Cells was Attenuated by HAS2 mRNA Knockdown In Examples 1-7 it was demonstrated that HAS2 is the dominant isoform responsible for increased HA synthesis by orbital fibroblasts in response to $PGD_2$. To test the involvement of HAS enzymes in the TGF-β mediated response, siRNA was used to selectively knock down HAS1 or HAS2 mRNA levels in fibroblasts. FIG. 15A shows that siRNA directed against HAS1 (open bars) or HAS2 (shaded bars) selectively and significantly reduced (by ~65-80% of mRNA levels) TGF-β-induced HAS1 and HAS2, compared with the scrambled control (SC) siRNA (black bars). In addition, the marked upregulation of secreted HA and pericellular HA in response to TGF-β1 was inhibited by HAS2 mRNA knockdown, but HAS1 knockdown had little effect (FIG. 15A). These data confirm the preceding examples showing that HAS2 is the dominant isoform in orbital fibroblasts. T cell adhesion to orbital fibroblasts that were untreated (open bars) or treated with TGF-β1 (black bars) after transfection with siRNAs for HAS1, HAS2 or SC siRNA was also analyzed. As expected, HAS2 knockdown significantly reduced T cell adhesion to orbital fibroblasts (FIG. 15B), further indicating that HA is required for T cell-orbital fibroblast adhesion.

Figure 16A:
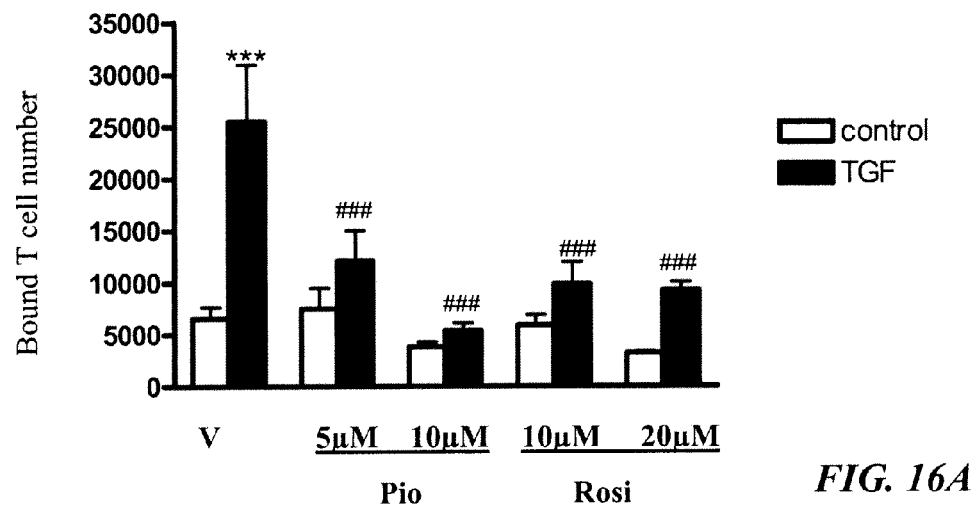
FIGS. 16A-B illustrate the ability of Pio and Rosi inhibit TGF-β1 induced peripheral blood T cell adhesion to orbital fibroblasts.
Figure 16B:
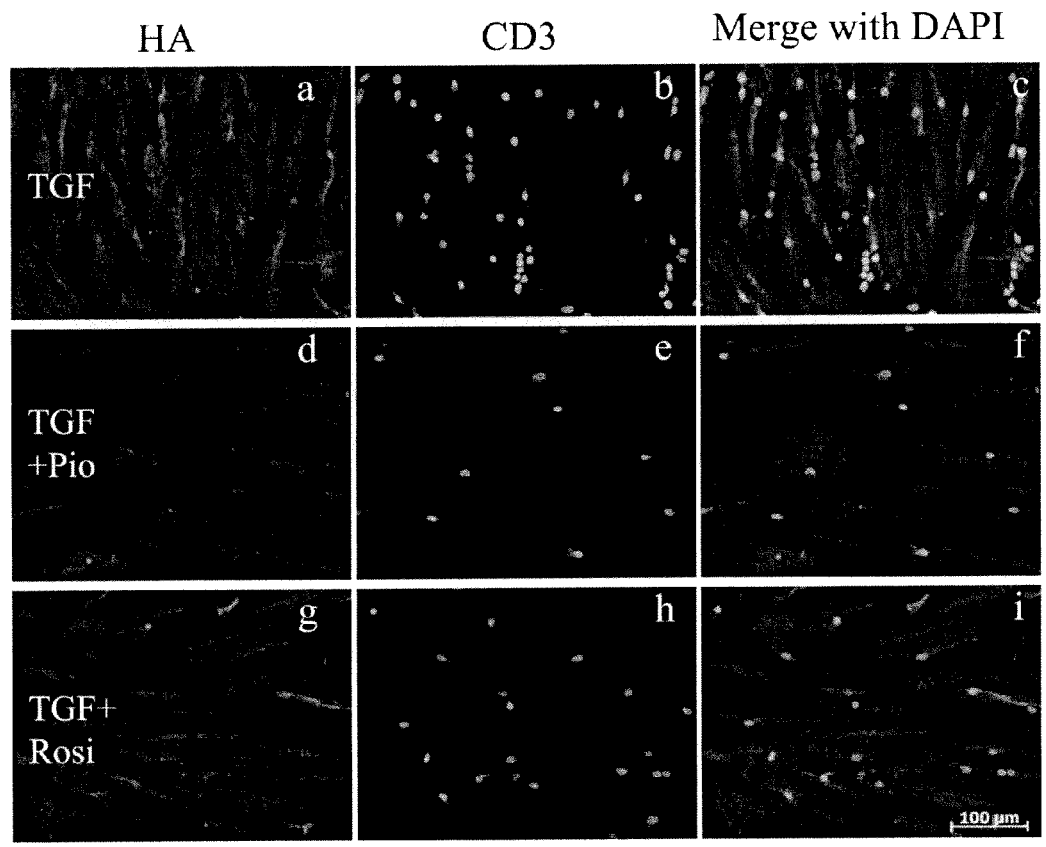

Example 14—Pio and Rosi Inhibit TGF-β1 Induced T-Cell Adhesion to Orbital Fibroblasts Since Pio and Rosi attenuate TGF-β1 induced HA synthesis, and HA mediates fibroblast and T cell adhesion, it was expected that Pio and Rosi might prevent TGF-β1 induced fibroblast-T cell adhesion. Fibroblasts were treated with different concentrations of Pio or Rosi together with TGF-β1. After 24 hours of treatment, the conditioned medium was removed to eliminate the influence of TGF-β1 and drugs on T cells and fresh medium was added along with the T cell suspension. As predicted, FIG. 16A demonstrates that fibroblasts pretreated with Pio or Rosi had significantly reduced ability to adhere to T cells compared to fibroblasts treated with TGF-β1 only. Immunostaining was used to confirm the adhesion assay results. T cells stained with the T cell marker CD3 (green) colocalize with fibroblasts and are associated with HA stained with biotinylated HABP (red) (FIG. 16B). TGF-β1 treated fibroblasts adhere to a greater number of T cells (FIG. 16B, panel c) than do TGF-β1 treated fibroblasts pretreated with Pio or Rosi (FIG. 16B, panel for i, respectively).

Example 15—$CD44^+/CD3^+$ Cells Infiltrate Graves' Orbital Adipose Tissue

Figure 17:
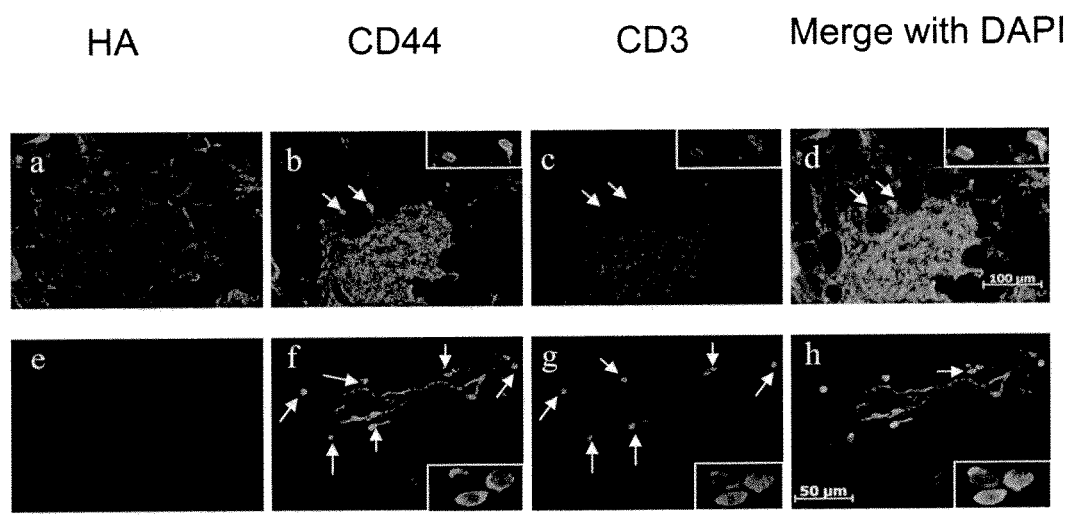
FIG. 17 is a panel of images showing that HA and CD3$^+$ T cells are present in orbital fat tissue from patients with TED. 10 μm thick sections of frozen Graves' orbital fat tissue were stained for HA with Biotinylated HABP (red, panels a, e), CD44 with anti-CD44 monoclonal antibody (green, panels b, f) and CD3 with anti-CD3 monoclonal antibody (purple, panels c, g). In panel e: addition of exogenous soluble free HA binds the HABP probe to remove endogenous HA signal. In panels d, h: merged fluorescence with DAPI staining. Representative immunofluorescence staining of T cell infiltration into orbital fat tissue of a patient with TED is shown.

The accumulation of GAGs and infiltration of inflammatory cells into orbital tissues are prominent histological markers of TED. The infiltration of T cells in Graves' orbital adipose tissue was further investigated using immunofluorescence on orbital tissue sections. Orbital adipose tissues were obtained from TED patients undergoing orbital decompression surgery as described in materials and methods. The tissue sections were stained with CD44 and CD3 antibodies, biotinylated HABP for HA staining, and DAPI for nuclear staining. FIG. 17 shows that CD44 (green) and CD3 (purple) are colocalized in small round cells (T cells). Concentrated infiltration of CD44⁺/CD3⁺ cells is visible in the adipose sections (FIG. 17, panels b, c, f and g). HA staining is shown by narrow red bands outlining large vacuoles that indicate fat droplet deposits (FIG. 17, panel a). Addition of free soluble HA to the HABP probe completely eliminated HA staining (FIG. 17, panel e), suggesting that the HA staining is specific. CD44⁺/CD3⁺ cells are clustered around the vessel area and are attached to the vessel wall or just outside the vessel, suggesting that CD44⁺/CD3⁺ cells were traversing through the vessel wall to the orbital tissue (FIG. 17, panels f and g, see arrows). Fat droplets were stained with Bodipy 493/503 dye and CD3⁺ cells could be found among the green fat droplets.

Discussion of Examples 8-15

Orbital fibroblasts are believed to be the primary autoimmune target in TED (Bahn, *N Engl J Med* 362(8):726-738 (2010); Bahn et al., *N Engl J Med.*, 329(20):1468-1475 (1993), each of which is hereby incorporated by reference in its entirety). Once orbital fibroblasts become activated, they undergo proliferation, differentiation and/or produce GAGs. The accumulation of GAGs, especially the hydrophilic GAG, HA, is the most evident feature of tissue remodeling in TED. Although TGF-β levels are increased in human orbital tissue and TGF-β increases HA secretion into the culture medium of orbital fibroblasts in vitro (van Steensel et al., *Invest Ophthalmol Vis Sci.* 50(7):3091-3098 (2009); Wang et al., *J Cell Biochem.* 95(2):256-67 (2005), each of which is hereby incorporated by reference in its entirety), the data presented in the preceding examples demonstrates for the first time that TGF-β induced accumulation of HA is not only secreted HA, but also pericellular HA (HA remaining on the cell surface). The increased HA levels mediated by TGF-β are most likely due to increased levels of HAS2 mRNA in orbital fibroblasts. Furthermore, TGF-β also increases the adhesion of activated T cells to orbital fibroblasts mediated by newly synthesized pericellular HA on orbital fibroblasts interacting with its cognate receptor CD44 on T cells.

The infiltration of orbital tissue by inflammatory cells (such as T cells, B cells, mast cells, and macrophages) and the accumulation of HA are two histological characteristics of TED (Lehmann et al., *Thyroid* 18(9):959-965 (2008), which is hereby incorporated by reference in its entirety). Surprisingly, the correlation between the two features is not clear. HA is a multifunctional ECM molecule that participates in regulation of inflammation and tissue remodeling. It is well documented that the HA-CD44 interaction can play a pro-inflammatory role in facilitating leukocyte recruitment and adhesion to inflammatory sites. Previous studies show that CD44 is expressed at elevated levels in Graves' orbital connective tissue in situ (Heufelder et al., *Med Klin* (Munich) 88(4):181-184, 277 (1993), which is hereby incorporated by reference in its entirety), suggesting a role for HA/CD44 in regulating inflammatory responses in TED. The results presented in the preceding examples demonstrate that CD44⁺ cells are present in Graves' orbital tissue sections and that these cells express the T cell marker CD3. These results also show that TGF-β induced HA-rich pericellular matrix facilitates orbital fibroblast adhesion to activated T cells. The adhesion of fibroblasts and T cells depends on the HA-CD44 interaction since: (1) activated human T cells highly express CD44 (FIG. 14A); (2) pre-incubation of T cells with CD44 antibody significantly reduced T cell adhesion to fibroblasts (FIG. 14B); (3) pre-treatment of the fibroblasts with *Streptomyces* hyaluronidase to digest HA diminished cell-cell adhesion (FIG. 14B); and (4) HAS2 siRNA blocked HA synthesis and significantly inhibited cell-cell adhesion (FIG. 15B); and (5) CD44⁺ T cells appear to attach to orbital fibroblasts with increases pericellular HA (FIG. 16B). Importantly, these data indicate that the accumulation of HA in orbital tissue not only contributes to periorbital edema, but also participates in the inflammatory response by enhancing or facilitating inflammatory cell infiltration into orbital tissue.

Recent work reveals that PPARγ and its ligands have anti-inflammatory and anti-TGF-β activities. Overexpression of PPARγ suppresses TGF-β-induced activation of monocytes/macrophages and fibrosis in human subconjunctival fibroblasts (Saika et al., *Am J Physiol Cell Physiol.* 293(1):C75-86 (2007); Yamanaka et al., *Invest Ophthalmol Vis Sci.* 50(1):187-193 (2009), each of which is hereby incorporated by reference in its entirety). TZDs and other PPARγ ligands such as 15d-PGJ₂ and CDDO, also show strong anti-TGF-β functions through PPARγ-dependent or independent pathways (Burgess et al., *Am J Physiol Lung Cell Mol Physiol.* 288(6):L1146-53 (2005); Ferguson et al., *Am J Respir Cell Mol Biol* 41:722-730 (2009); Guo et al., *Diabetes* 53(1):200-208 (2004), each of which is hereby incorporated by reference in its entirety). Circulating levels of the chemokine CXCL10 and the cytokine interferon gamma (IFNγ) are elevated in patients with Graves' Disease, particularly in those with active TED. Rosi and Pio exert a dose-dependent inhibition of IFNγ and Tumor Necrosis Factor-alpha (TNFα)-induced chemokines CXCL9, CXCL10 and CXCL11 secretion in orbital fibroblasts, preadipocytes and thyrocytes (Antonelli et al., *J Clin Endocrinol Metab.* 91(2):614-620 (2006); Antonelli et al., *J Clin Endocrinol Metab* 94(5):1803-1809 (2009), which is hereby incorporated by reference in its entirety). While these studies indicate that PPARγ activity is involved in the regulation of IFNγ induced chemokine expression in thyroid autoimmunity and TED, and PPARγ activators might attenuate the recruitment of activated T cells at sites of T helper type 1 (Th1)-mediated inflammation, the preceding examples quite surprisingly demonstrate that the activity of PPARγ ligands Pio and Rosi in the context of the present invention occurs via a PPARγ-independent mechanism.

Both Pio and Rosi inhibit TGF-β mediated functions including: elevating HAS1 and HAS2 mRNA levels, HA production, and T cell-fibroblast adhesion. However, in the experimental systems employed neither a PPARγ antagonist GW9662 nor PPARγ knockdown relieve the inhibition of HA induction by Pio and Rosi. The possibility of a PPARγ-independent mechanism for the Pio and Rosi mediated reduction of TGF-β activity was unexpected. Therefore, several signaling pathways were evaluated to identify a potential mechanism whereby TGF-β driven HA synthesis is inhibited by Pio and Rosi in the experimental system employed. However, there was no clear evidence showing that Pio or Rosi are general inhibitors of TGF-β-induced responses in orbital fibroblasts. For example, the phosphorylation and nuclear translocation of Smad2 and 3 induced by TGF-β was unaffected by co-treatment with Pio or Rosi. Furthermore, Pio and Rosi did not inhibit the TGF-β-activated mitogen-activated protein kinase (MAPK) signaling pathway or the phosphorylation of p38 and p42/44. Other alternative pathways of TGF-β such as phosphorylation of AKT, c-jun N-terminal kinase (JNK) or c-Abl were not detectable after TGF-β treatment in orbital fibroblast.

Despite these results, several case reports have described development of exophthalmos in patients receiving TZD treatment for type 2 diabetes (Levin et al., *Arch Ophthalmol* 123(1):119-121 (2005); Lee et al., *BMC Ophthalmol* 7:8. (2007); Dorkhan et al., *Clin Endocrinol* (Oxf) 65(1):35-39 (2006); Starkey et al., *J Clin Endocrinol Metab* 88(1):55-59 (2003), each of which is hereby incorporated by reference in its entirety). Since the results of these clinical studies are from TED patients with type 2 diabetes, the increase in exophthalmos might be the result of adipocyte accumulation due to a pre-existing hyperinsulinaemic state (Dorkhan et al., *Clin Endocrinol* (Oxf) 65(1):35-39 (2006), which is hereby incorporated by reference in its entirety). Furthermore, the success of TZD drugs as a therapy for type 2 diabetes is also paradoxical, as they target PPARγ, which induces adipose tissue formation, a major risk factor for type 2 diabetes (Lehrke et al., *Cell* 123(6):993-999 (2005), which is hereby incorporated by reference in its entirety).

Taken together, Examples 8-15 demonstrate that TGF-β plays an important role in human orbital fibroblast HA synthesis and the accumulation of HA in orbital tissue not only contributes to periorbital edema, but also participates in inflammatory responses by enhancing or facilitating inflammatory cell infiltration into orbital tissue. Furthermore, the PPARγ ligands Pio and Rosi have strong inhibitory effects on TGF-β-mediated inflammatory processes and their mode of action is PPARγ-independent. Because these PPARγ ligands operate by a different mechanism in down-regulating HA expression, these and other PPARγ ligands may be especially useful in combination therapies with one or more of HAS2 RNAi, an inhibitor of PGDS, and a DP1 antagonist for the treatment or prevention of TED.

Example 16—15-Deoxy-Δ12,14-Prostaglandin J2 (15d-PGD2) Inhibits TGF-β1 Induced HA Secretion in a Dose-Dependent Manner 15-deoxy-Δ12,14-Prostaglandin J2 (15d-PGD2) is an endogenous PPARγ ligand that exhibits diverse biological effects, including anti-inflammatory and anti-fibrogenic activities. Given the demonstrated results in the preceding examples, in this example it is demonstrated that 15d-PGD2 inhibits TGF-β-mediated HA secretion in orbital fibroblasts.

Figure 18:
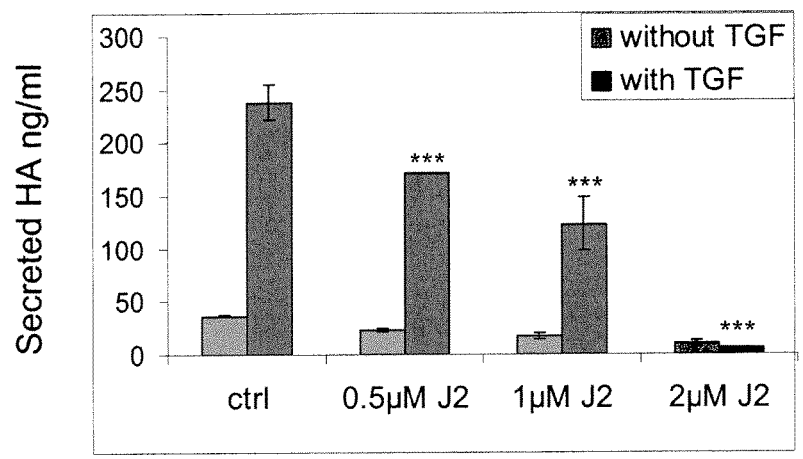
FIG. 18 is a graph illustrating the ability of 15d-PGJ2 inhibits TGF-beta induced HA production (***$p<0.001$ compared to vehicle control).

Primary orbital fibroblasts were isolated from Graves' disease patients undergoing orbital decompression surgery. The cells were grown in RPMI 1640 media containing 10% FBS, and incubated for 24 hours either with or without 2 ng/ml TGF-β1, and 0.5 µM, 1.0 µM, or 2.0 µM 15d-PGD2. The amount of HA in the cell culture supernatant and pericellular extraction was measured by ELISA as in the preceding Examples. While 15d-PGD2 enhanced TGF-β induced HAS1 mRNA expression, it inhibited TGF-β induced HAS2 mRNA expression. While TGF-β normally induces both HAS1 and HAS2 mRNA expression, TGF-β induced HA secretion was inhibited by 15d-PGJ2 (FIG. 18). Similar results were obtained with respect to pericellular HA.

These data reveal that 15d-PGJ2 is a potent inhibitor of TGF-β mediated pro-inflammatory and fibrogenic activities in orbital fibroblasts. Newly synthesized HA plays an impotent role in T cell-fibroblast adhesion. The ability to block HA synthesis with inhibitors such as 15d-PGJ2, therefore, presents an additional agent for therapeutic treatment of TED.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of treating thyroid eye disease comprising: selecting a patient having thyroid eye disease and administering to the selected patient a composition comprising an agent that interferes with hyaluronan synthesis in an amount that is effective to inhibit hyaluronan synthesis in a retro-ocular space, wherein the agent is 4-benzhydryloxy-1-[3-(1H-tetrazol-5-yl)-propyl]-piperidine (HQL-79), ethyl 3-(2-(3-fluorophenyl)pyrimidine-5-carboxamido)pyrrolidine-1-carboxylate, N-(1-(7,8-dihydro-5H-pyrano[4,3-d]pyrimidin-2-yl)pyrrolidin-3-yl)-2-(3-fluorophenyl)pyrimidine-5-carboxamide, 2-(3-fluorophenyl)-N-{1-[(methylamino)carbonyl]piperidin-4-yl}pyrimidine-5-carboxamide, 2-(3-fluorophenyl)-N-[1-(6-methyl-5,6,7,8-tetrahydropyrido[4,3-d]pyrimidin-2-yl)pyrrolidin-3-yl]pyrimidine-5-carboxamide, or 2-(3-fluorophenyl)-N-[1-(2,2,2-trifluoroethyl)piperidin-4-yl]pyrimidine-5-carboxamide.

2. The method according to claim 1, wherein the composition comprises a PPARγ ligand, wherein the PPARγ ligand is 15-deoxy-Δ12,14-Prostaglandin J2 or a thiazolidinedione.

3. The method according to claim 1, wherein said administering is carried out by injecting the agent into the retro-ocular space or application of a composition comprising the agent onto a surface of the patient's eye.

4. The method according to claim 1, wherein the composition is a pharmaceutical composition further comprising a carrier selected from the group consisting of a liquid, suspension, polymeric delivery vehicle, mucoadhesive substance, and nanosphere.

5. The method according to claim 1, wherein the agent that interferes with hyaluronan synthesis is 4-benzhydryloxy-1-[3-(1H-tetrazol-5-yl)-propyl]-piperidine (HQL-79).

* * * * *